(12) United States Patent
Basile et al.

(10) Patent No.: US 8,790,652 B2
(45) Date of Patent: Jul. 29, 2014

(54) USE OF THE COMBINATION OF SEMAPHORIN-4D INHIBITORY MOLECULES AND VEGF INHIBITORY MOLECULES TO INHIBIT ANGIOGENESIS

(71) Applicant: Vaccinex, Inc., Rochester, NY (US)

(72) Inventors: John R. Basile, Kensington, MD (US); Elizabeth E. Evans, Bloomfield, NY (US); Ernest S. Smith, Ontario, NY (US)

(73) Assignee: Vaccinex, Inc., Rochester, NY (US)

( * ) Notice: Subject to any disclaimer, the term of this patent is extended or adjusted under 35 U.S.C. 154(b) by 0 days.

(21) Appl. No.: 13/707,299

(22) Filed: Dec. 6, 2012

(65) Prior Publication Data

US 2013/0142810 A1 Jun. 6, 2013

Related U.S. Application Data

(60) Provisional application No. 61/567,531, filed on Dec. 6, 2011, provisional application No. 61/576,188, filed on Dec. 15, 2011.

(51) Int. Cl.
*A61K 39/395* (2006.01)
*C07K 16/28* (2006.01)

(52) U.S. Cl.
USPC ............... 424/145.1; 424/133.1; 424/134.1; 424/136.1; 424/158.1

(58) Field of Classification Search
None
See application file for complete search history.

(56) References Cited

U.S. PATENT DOCUMENTS

| | | | |
|---|---|---|---|
| 6,884,879 B1 | 4/2005 | Baca et al. | |
| 7,060,269 B1 | 6/2006 | Baca et al. | |
| 7,169,901 B2 | 1/2007 | Baca et al. | |
| 2006/0233793 A1 | 10/2006 | Belin et al. | |
| 2007/0148177 A1 | 6/2007 | Fyfe et al. | |
| 2007/0154483 A1 | 7/2007 | Fyfe et al. | |
| 2008/0219971 A1 | 9/2008 | Smith et al. | |
| 2010/0285036 A1* | 11/2010 | Smith et al. | ............ 424/172.1 |
| 2012/0270268 A1 | 10/2012 | Smith et al. | |
| 2013/0095118 A1 | 4/2013 | Smith et al. | |

FOREIGN PATENT DOCUMENTS

| | | |
|---|---|---|
| WO | WO 93/14125 | 7/1993 |
| WO | WO 2005/000900 A1 | 1/2005 |
| WO | WO 2008/100995 A1 | 8/2008 |
| WO | WO 2010/129917 A1 | 11/2010 |
| WO | WO 2011/159704 A1 | 12/2011 |

OTHER PUBLICATIONS

Yu et al., Investigative Ophthalmology & Visual Science 49(2): 522-527, Feb. 2008.*
Witte et al., Cancer and Metastasis Reviews 17: 155-161, 1998.*
Fonsatti et al., J Translational Medicine 2: 18, 2004.*
Stancovski et al., Proceedings of the National Academy of Science USA 88: 8691-8695, 1991.*
Cheung et al., Pharmacotherapy 2013, [Epub ahead of print], 18 pages.*
Riemer et al., Mol. Immunol. 42: 1121-1124, 2005.*
Rudikoff et al., Proc. Natl. Acad. Sci. USA, 79(6): 1979-1983, Mar. 1982.*
Colman et al., Research in Immunology, 145:33-36, 1994.*
MacCallum et al., J. Mol. Biol., 262, 732-745, 1996.*
Wu et al., J. Mol. Biol. 294: 151-162, 1999.*
Bussolino, F., et al., "Molecular mechanisms of blood vessel formation," *Trends Biochem. Sci.* 22(7):251-256, Elsevier Trends Journals, England (1997).
Carmeliet, P., "Angiogenesis in health and disease," *Nat. Med.* 9(6):653-660, Nature Publishing Company, United States (2003).
DeLaire, S., et al., "Biological Activity of Soluble CD100. II. Soluble CD100, Similarly to H-SemaIII, Inhibits Immune Cell Migration," *J. Immunol.* 166:4348-4354, The American Association of Immunologists, United States (2001).
Dougher, M. and Terman, B.I., "Autophosphorylation of KDR in the kinase domain is required for maximal VEGF-stimulated kinase activity and receptor internalization," *Oncogene* 18(8):1619-1627, Nature Publishing Group, England (1999).
Elhabazi, A., et al., "Biological Actvity of Soluble CD100. I. The Extracellular Region of CD100 Is Released from the Surface of T Lymphocytes by Regulated Proteolysis," *J. Immunol.* 166:4341-4347, The American Association of Immunologists, Inc., United States (2001).
Ferrara, N., "VEGF and the quest for tumour angiogenesis factors," *Nat. Rev. Cancer* 2(10):795-803, Nature Pub. Group, England (2002).
Ferrara, N., et al., "The biology of VEGF and its receptors," *Nat. Med.* 9(6):669-676, Nature Publishing Company, United States (2003).
Gerber, H.P. and Ferrara, N., "Pharmacology and pharmacodynamics of bevacizumab as monotherapy or in combination with cytotoxic therapy in preclinical studies," *Cancer Res* 65(3):671-680, American Association for Cancer Research, United States (2005).
Giraudon, P., et al., "Semaphorin CD100 from Activated T Lymphotcytes Induces Process Extension Collapse in Oligodendrocytes and Death of Immature Neural Cells," *J. Immunol.* 172:1246-1255, The American Assoication of Immunologists, Inc., United States (2004).
Giraudon, P., et al., "T-Cells in Neuronal Injury and Repair," *NeuroMolecular Medicine* 7:207-216, Humana Press, United States (2005).
Herold, C., et al., "Activation signals are delivered through two distinct epitopes of CD100, a unique 150 kDa human lymphocyte surface structure previously defined by BB18 mAb," *Int. Immunol.* 7(1):1-8, Oxford University Press, England (1994).
Hicklin, D.J. and Ellis, L.M., "Role of the vascular endothelial growth factor pathway in tumor growth and angiogenesis," *J. Clin. Oncol.* 23(5):1011-1027, American Society of Clinical Oncology, United States (2005).
Ho, Q.T. and Kuo, C.J., "Vascular endothelial growth factor: biology and therapeutic applications," *Int. J. Biochem. Cell Biol.* 39(7-8):1349-1357, Elsevier, Netherlands (2007).

(Continued)

*Primary Examiner* — Phuong Huynh
(74) *Attorney, Agent, or Firm* — Thompson Coburn LLP

(57) ABSTRACT

Provided herein are methods for inhibiting tumor angiogenesis in a cancer patient, the method comprising administering to the subject an effective amount of a first isolated binding molecule which specifically binds to semaphorin-4D (SEMA4D) and an effective amount of a second isolated binding molecule which specifically binds to VEGF.

22 Claims, 3 Drawing Sheets

(56) References Cited

OTHER PUBLICATIONS

Figure 1:
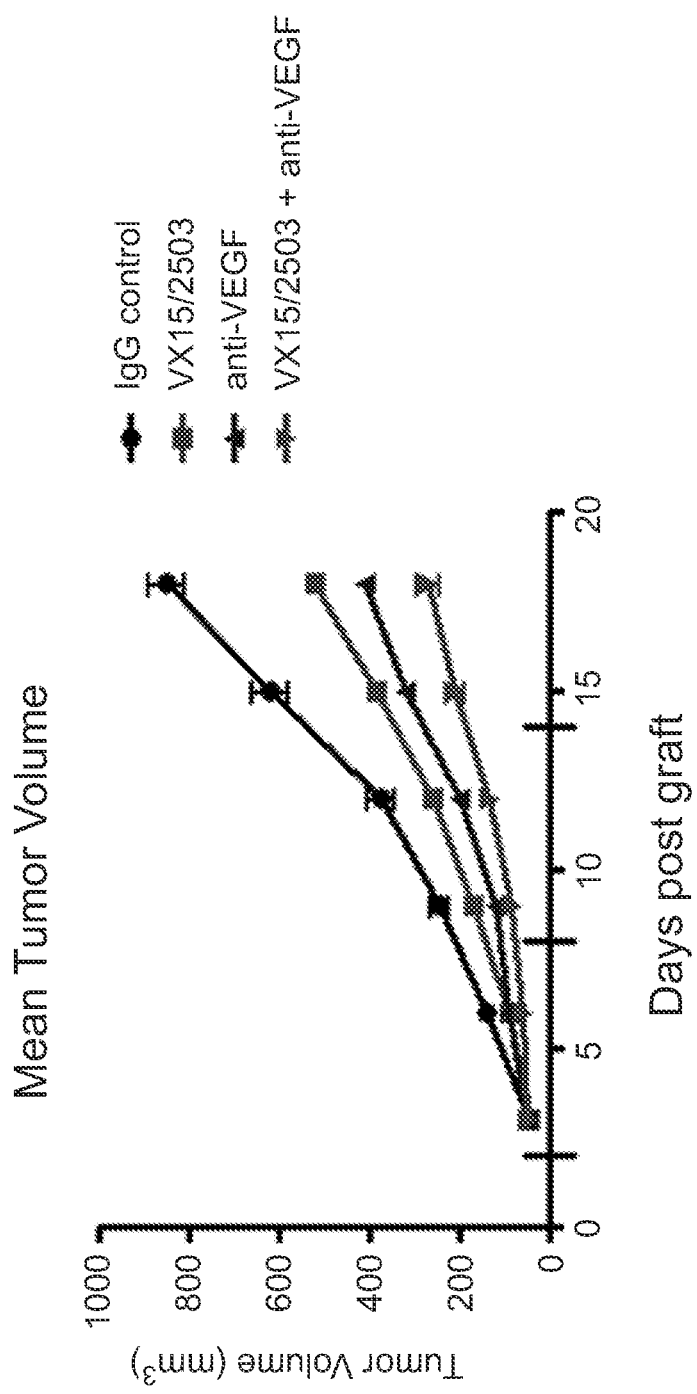

Ishida, I., et al., "Involvement of CD100, a lymphocyte semaphoring, in the activation of the human immune system via CD72: implications for the regulation of immune and inflammatory responses," *Int. Immunol.* 15(8):1027-1034, The Japanese Society for Immunology, Japan (2003).

Jain, R.K., "Molecular regulation of vessel maturation," *Nat Med.* 9(6):685-693, Nature Publishing Company, United States (2003).

Kikutani, H. and Kumanogoh, A., "Semaphorins in interactions between T cells and antigen-presenting cells," *Nat. Rev. Immunol.* 3(2):159-167, Nature Pub. Group, England (2003).

Kim, K.J., et al., "Inhibition of vascular endothelial growth factor-induced angiogenesis suppresses tumour growth in vivo," *Nature* 362(6423):841-844, Nature Publishing Group, England (1993).

Kruger, R.P., "Semaphorins Command Cells to Move," *Nat. Rev. Mol. Cell Biol.* 6:789-800, Nature Pub. Group, England (2005).

Kumanogoh, A., "Identification of CD72 as a Lymphocyte Receptor for the Class IV Semaphorin CD100: A Novel Mechanism for Regulating B Cell Signaling," *Immunity* 13:621-631, Cell Press, United States (2000).

Kumanogoh, A. and Kikutani, H., "The CD100-CD72 interaction: a novel mechanism of immune regulation," *TRENDS in Immunology* 22(12):670-676, Elsevier Science Ltd., England (2001).

Kumanogoh, A., et al., "Requirement for the Lymphocyte Semaphorin, CD100, in the Induction of Antigen-Specific T Cells and the Maturation of Dendritic Cells," *J. Immunol.* 169:1175-1181, The American Association of Immunologists, United States (2002).

Kumanogoh, A. and Kikutani, H., "Immune semaphorins: a new area of semaphorin research," *J. Cell Science* 116(17):3463-3470, The Company of Biologists Ltd., England (2003).

Pander, J., et al., "Pharmacogenetics of EGFR and VEGF inhibition," *Drug Discov. Today* 12(23-24):1054-1060, Elsevier Science Ltd., England (2007).

Pastercamp, R.J., "R-Ras fills another GAP in semaphoring signaling," *TRENDS in Cell Biology* 15(2):61-64, Elsevier Science Publishers, England (2005).

Presta, L.G., et al., "Humanization of an anti-vascular endothelial growth factor monoclonal antibody for the therapy of solid tumors and other disorders," *Cancer Res.* 57(20):4593-4599, American Association for Cancer Research, United States (1997).

Risau, W., "Mechanisms of angiogenesis," *Nature* 386(6626):671-674, Nature Publishing Group, England (1997).

Shi, W., et al., "The Class IV Semaphorin CD100 Plays Nonredundant Roles in the Immune System: Defective B and T Cell Activiation in CD100-Deficient Mice," *Immunity* 13:633-642, Cell Press, United States (2000).

Sierra, J.R., et al., "Tumor angiogenesis and progression are enhanced by Sema4D produced by tumor-associated macrophages," *J. Exp. Med.* 205(7):1673-1685, Rockefeller University Press, United States (2008).

Suzuki, K., et al., "Semaphorins and their receptors in immune cell interactions," *Nat. Immunol.* 9(1):17-23, Nature America Inc., United States (2008).

Tamagnone, L., "Plexins Are a Large Family of Receptors for Transmembrane, Secreted, and GPI-Anchored Semaphorins in Vertebrates," *Cell* 99:71-80, Cell Press, United States (1999).

Wang, X., et al., "Functional soluble CD100/Sema4D released from activated lymphocytes: possible role in normal and pathologic immune responses," *Blood* 97:3498-3504, The American Society of Hematology, United States (2011).

Watanabe, C., et al., "Enhanced Immune Responses in Transgenic Mice Expressing a Truncated Form of the Lymphocyte Semaphorin CD100," *J. Immunol.* 167:4321-4328, The American Association of Immunologists, United States (2001).

\* cited by examiner

SEQUENCE LISTING

```
<160> NUMBER OF SEQ ID NOS: 56

<210> SEQ ID NO 1
<211> LENGTH: 862
<212> TYPE: PRT
<213> ORGANISM: Homo sapiens

<400> SEQUENCE: 1

Met Arg Met Cys Thr Pro Ile Arg Gly Leu Leu Met Ala Leu Ala Val
1               5                   10                  15

Met Phe Gly Thr Ala Met Ala Phe Ala Pro Ile Pro Arg Ile Thr Trp
            20                  25                  30

Glu His Arg Glu Val His Leu Val Gln Phe His Glu Pro Asp Ile Tyr
        35                  40                  45

Asn Tyr Ser Ala Leu Leu Leu Ser Glu Asp Lys Asp Thr Leu Tyr Ile
    50                  55                  60

Gly Ala Arg Glu Ala Val Phe Ala Val Asn Ala Leu Asn Ile Ser Glu
65                  70                  75                  80

Lys Gln His Glu Val Tyr Trp Lys Val Ser Glu Asp Lys Lys Ala Lys
                85                  90                  95

Cys Ala Glu Lys Gly Lys Ser Lys Gln Thr Glu Cys Leu Asn Tyr Ile
            100                 105                 110

Arg Val Leu Gln Pro Leu Ser Ala Thr Ser Leu Tyr Val Cys Gly Thr
        115                 120                 125
```

```
Asn Ala Phe Gln Pro Ala Cys Asp His Leu Asn Leu Thr Ser Phe Lys
        130                 135                 140

Phe Leu Gly Lys Asn Glu Asp Gly Lys Gly Arg Cys Pro Phe Asp Pro
145                 150                 155                 160

Ala His Ser Tyr Thr Ser Val Met Val Asp Gly Glu Leu Tyr Ser Gly
                165                 170                 175

Thr Ser Tyr Asn Phe Leu Gly Ser Glu Pro Ile Ile Ser Arg Asn Ser
                180                 185                 190

Ser His Ser Pro Leu Arg Thr Glu Tyr Ala Ile Pro Trp Leu Asn Glu
        195                 200                 205

Pro Ser Phe Val Phe Ala Asp Val Ile Arg Lys Ser Pro Asp Ser Pro
210                 215                 220

Asp Gly Glu Asp Asp Arg Val Tyr Phe Phe Thr Glu Val Ser Val
225                 230                 235                 240

Glu Tyr Glu Phe Val Phe Arg Val Leu Ile Pro Arg Ile Ala Arg Val
                245                 250                 255

Cys Lys Gly Asp Gln Gly Gly Leu Arg Thr Leu Gln Lys Lys Trp Thr
                260                 265                 270

Ser Phe Leu Lys Ala Arg Leu Ile Cys Ser Arg Pro Asp Ser Gly Leu
        275                 280                 285

Val Phe Asn Val Leu Arg Asp Val Phe Val Leu Arg Ser Pro Gly Leu
        290                 295                 300

Lys Val Pro Val Phe Tyr Ala Leu Phe Thr Pro Gln Leu Asn Asn Val
305                 310                 315                 320

Gly Leu Ser Ala Val Cys Ala Tyr Asn Leu Ser Thr Ala Glu Glu Val
                325                 330                 335

Phe Ser His Gly Lys Tyr Met Gln Ser Thr Val Glu Gln Ser His
                340                 345                 350

Thr Lys Trp Val Arg Tyr Asn Gly Pro Val Pro Lys Pro Arg Pro Gly
        355                 360                 365

Ala Cys Ile Asp Ser Glu Ala Arg Ala Ala Asn Tyr Thr Ser Ser Leu
        370                 375                 380

Asn Leu Pro Asp Lys Thr Leu Gln Phe Val Lys Asp His Pro Leu Met
385                 390                 395                 400

Asp Asp Ser Val Thr Pro Ile Asp Asn Arg Pro Arg Leu Ile Lys Lys
                405                 410                 415

Asp Val Asn Tyr Thr Gln Ile Val Val Asp Arg Thr Gln Ala Leu Asp
                420                 425                 430

Gly Thr Val Tyr Asp Val Met Phe Val Ser Thr Asp Arg Gly Ala Leu
        435                 440                 445

His Lys Ala Ile Ser Leu Glu His Ala Val His Ile Ile Glu Glu Thr
        450                 455                 460

Gln Leu Phe Gln Asp Phe Glu Pro Val Gln Thr Leu Leu Ser Ser
465                 470                 475                 480

Lys Lys Gly Asn Arg Phe Val Tyr Ala Gly Ser Asn Ser Gly Val Val
                485                 490                 495

Gln Ala Pro Leu Ala Phe Cys Gly Lys His Gly Thr Cys Glu Asp Cys
                500                 505                 510

Val Leu Ala Arg Asp Pro Tyr Cys Ala Trp Ser Pro Pro Thr Ala Thr
        515                 520                 525

Cys Val Ala Leu His Gln Thr Glu Ser Pro Ser Arg Gly Leu Ile Gln
        530                 535                 540
```

```
Glu Met Ser Gly Asp Ala Ser Val Cys Pro Asp Lys Ser Lys Gly Ser
545                 550                 555                 560

Tyr Arg Gln His Phe Phe Lys His Gly Gly Thr Ala Glu Leu Lys Cys
                565                 570                 575

Ser Gln Lys Ser Asn Leu Ala Arg Val Phe Trp Lys Phe Gln Asn Gly
            580                 585                 590

Val Leu Lys Ala Glu Ser Pro Lys Tyr Gly Leu Met Gly Arg Lys Asn
        595                 600                 605

Leu Leu Ile Phe Asn Leu Ser Glu Gly Asp Ser Gly Val Tyr Gln Cys
    610                 615                 620

Leu Ser Glu Glu Arg Val Lys Asn Lys Thr Val Phe Gln Val Val Ala
625                 630                 635                 640

Lys His Val Leu Glu Val Lys Val Val Pro Lys Pro Val Val Ala Pro
                645                 650                 655

Thr Leu Ser Val Val Gln Thr Glu Gly Ser Arg Ile Ala Thr Lys Val
                660                 665                 670

Leu Val Ala Ser Thr Gln Gly Ser Ser Pro Pro Thr Pro Ala Val Gln
            675                 680                 685

Ala Thr Ser Ser Gly Ala Ile Thr Leu Pro Pro Lys Pro Ala Pro Thr
        690                 695                 700

Gly Thr Ser Cys Glu Pro Lys Ile Val Ile Asn Thr Val Pro Gln Leu
705                 710                 715                 720

His Ser Glu Lys Thr Met Tyr Leu Lys Ser Ser Asp Asn Arg Leu Leu
                725                 730                 735

Met Ser Leu Phe Leu Phe Phe Val Leu Phe Leu Cys Leu Phe Leu Phe
                740                 745                 750

Tyr Asn Cys Tyr Lys Gly Tyr Leu Pro Arg Gln Cys Leu Lys Phe Arg
            755                 760                 765

Ser Ala Leu Leu Ile Gly Lys Lys Pro Lys Ser Asp Phe Cys Asp
        770                 775                 780

Arg Glu Gln Ser Leu Lys Glu Thr Leu Val Glu Pro Gly Ser Phe Ser
785                 790                 795                 800

Gln Gln Asn Gly Glu His Pro Lys Pro Ala Leu Asp Thr Gly Tyr Glu
                805                 810                 815

Thr Glu Gln Asp Thr Ile Thr Ser Lys Val Pro Thr Asp Arg Glu Asp
                820                 825                 830

Ser Gln Arg Ile Asp Asp Leu Ser Ala Arg Asp Lys Pro Phe Asp Val
            835                 840                 845

Lys Cys Glu Leu Lys Phe Ala Asp Ser Asp Ala Asp Gly Asp
850                 855                 860

<210> SEQ ID NO 2
<211> LENGTH: 861
<212> TYPE: PRT
<213> ORGANISM: Murine sp.

<400> SEQUENCE: 2

Met Arg Met Cys Ala Pro Val Arg Gly Leu Phe Leu Ala Leu Val Val
1               5                   10                  15

Val Leu Arg Thr Ala Val Ala Phe Ala Pro Val Pro Arg Leu Thr Trp
            20                  25                  30

Glu His Gly Glu Val Gly Leu Val Gln Phe His Lys Pro Gly Ile Phe
        35                  40                  45

Asn Tyr Ser Ala Leu Leu Met Ser Glu Asp Lys Asp Thr Leu Tyr Val
    50                  55                  60
```

```
Gly Ala Arg Glu Ala Val Phe Ala Val Asn Ala Leu Asn Ile Ser Glu
65                  70                  75                  80

Lys Gln His Glu Val Tyr Trp Lys Val Ser Glu Asp Lys Lys Ser Lys
                85                  90                  95

Cys Ala Glu Lys Gly Lys Ser Lys Gln Thr Glu Cys Leu Asn Tyr Ile
            100                 105                 110

Arg Val Leu Gln Pro Leu Ser Thr Ser Leu Tyr Val Cys Gly Thr
        115                 120                 125

Asn Ala Phe Gln Pro Thr Cys Asp His Leu Asn Leu Thr Ser Phe Lys
130                 135                 140

Phe Leu Gly Lys Ser Glu Asp Gly Lys Gly Arg Cys Pro Phe Asp Pro
145                 150                 155                 160

Ala His Ser Tyr Thr Ser Val Met Val Gly Gly Glu Leu Tyr Ser Gly
                165                 170                 175

Thr Ser Tyr Asn Phe Leu Gly Ser Glu Pro Ile Ile Ser Arg Asn Ser
            180                 185                 190

Ser His Ser Pro Leu Arg Thr Glu Tyr Ala Ile Pro Trp Leu Asn Glu
        195                 200                 205

Pro Ser Phe Val Phe Ala Asp Val Ile Gln Lys Ser Pro Asp Gly Pro
210                 215                 220

Glu Gly Glu Asp Asp Lys Val Tyr Phe Phe Thr Glu Val Ser Val
225                 230                 235                 240

Glu Tyr Glu Phe Val Phe Lys Leu Met Ile Pro Arg Val Ala Arg Val
                245                 250                 255

Cys Lys Gly Asp Gln Gly Gly Leu Arg Thr Leu Gln Lys Lys Trp Thr
            260                 265                 270

Ser Phe Leu Lys Ala Arg Leu Ile Cys Ser Lys Pro Asp Ser Gly Leu
        275                 280                 285

Val Phe Asn Ile Leu Gln Asp Val Phe Val Leu Arg Ala Pro Gly Leu
290                 295                 300

Lys Glu Pro Val Phe Tyr Ala Val Phe Thr Pro Gln Leu Asn Asn Val
305                 310                 315                 320

Gly Leu Ser Ala Val Cys Ala Tyr Thr Leu Ala Thr Val Glu Ala Val
                325                 330                 335

Phe Ser Arg Gly Lys Tyr Met Gln Ser Ala Thr Val Glu Gln Ser His
            340                 345                 350

Thr Lys Trp Val Arg Tyr Asn Gly Pro Val Pro Thr Pro Arg Pro Gly
        355                 360                 365

Ala Cys Ile Asp Ser Glu Ala Arg Ala Ala Asn Tyr Thr Ser Ser Leu
370                 375                 380

Asn Leu Pro Asp Lys Thr Leu Gln Phe Val Lys Asp His Pro Leu Met
385                 390                 395                 400

Asp Asp Ser Val Thr Pro Ile Asp Asn Arg Pro Lys Leu Ile Lys Lys
                405                 410                 415

Asp Val Asn Tyr Thr Gln Ile Val Val Asp Arg Thr Gln Ala Leu Asp
            420                 425                 430

Gly Thr Phe Tyr Asp Val Met Phe Ile Ser Thr Asp Arg Gly Ala Leu
        435                 440                 445

His Lys Ala Val Ile Leu Thr Lys Glu Val His Val Ile Glu Glu Thr
        450                 455                 460

Gln Leu Phe Arg Asp Ser Glu Pro Val Leu Thr Leu Leu Leu Ser Ser
465                 470                 475                 480
```

Lys Lys Gly Arg Lys Phe Val Tyr Ala Gly Ser Asn Ser Gly Val Val
            485                 490                 495

Gln Ala Pro Leu Ala Phe Cys Glu Lys His Gly Ser Cys Glu Asp Cys
        500                 505                 510

Val Leu Ala Arg Asp Pro Tyr Cys Ala Trp Ser Pro Ala Ile Lys Ala
        515                 520                 525

Cys Val Thr Leu His Gln Glu Ala Ser Ser Arg Gly Trp Ile Gln
        530                 535                 540

Asp Met Ser Gly Asp Thr Ser Ser Cys Leu Asp Lys Ser Lys Glu Ser
545                 550                 555                 560

Phe Asn Gln His Phe Phe Lys His Gly Gly Thr Ala Glu Leu Lys Cys
                565                 570                 575

Phe Gln Lys Ser Asn Leu Ala Arg Val Val Trp Lys Phe Gln Asn Gly
            580                 585                 590

Glu Leu Lys Ala Ala Ser Pro Lys Tyr Gly Phe Val Gly Arg Lys His
        595                 600                 605

Leu Leu Ile Phe Asn Leu Ser Asp Gly Asp Ser Gly Val Tyr Gln Cys
        610                 615                 620

Leu Ser Glu Glu Arg Val Arg Asn Lys Thr Val Ser Gln Leu Leu Ala
625                 630                 635                 640

Lys His Val Leu Glu Val Lys Met Val Pro Arg Thr Pro Ser Pro
                645                 650                 655

Thr Ser Glu Asp Ala Gln Thr Glu Gly Ser Lys Ile Thr Ser Lys Met
                660                 665                 670

Pro Val Ala Ser Thr Gln Gly Ser Ser Pro Thr Pro Ala Leu Trp
        675                 680                 685

Ala Thr Ser Pro Arg Ala Ala Thr Leu Pro Pro Lys Ser Ser Ser Gly
        690                 695                 700

Thr Ser Cys Glu Pro Lys Met Val Ile Asn Thr Val Pro Gln Leu His
705                 710                 715                 720

Ser Glu Lys Thr Val Tyr Leu Lys Ser Ser Asp Asn Arg Leu Leu Met
                725                 730                 735

Ser Leu Leu Leu Phe Ile Phe Val Leu Phe Leu Cys Leu Phe Ser Tyr
            740                 745                 750

Asn Cys Tyr Lys Gly Tyr Leu Pro Gly Gln Cys Leu Lys Phe Arg Ser
        755                 760                 765

Ala Leu Leu Leu Gly Lys Lys Thr Pro Lys Ser Asp Phe Ser Asp Leu
        770                 775                 780

Glu Gln Ser Val Lys Glu Thr Leu Val Glu Pro Gly Ser Phe Ser Gln
785                 790                 795                 800

Gln Asn Gly Asp His Pro Lys Pro Ala Leu Asp Thr Gly Tyr Glu Thr
                805                 810                 815

Glu Gln Asp Thr Ile Thr Ser Lys Val Pro Thr Asp Arg Glu Asp Ser
            820                 825                 830

Gln Arg Ile Asp Glu Leu Ser Ala Arg Asp Lys Pro Phe Asp Val Lys
        835                 840                 845

Cys Glu Leu Lys Phe Ala Asp Ser Asp Ala Asp Gly Asp
        850                 855                 860

<210> SEQ ID NO 3
<211> LENGTH: 30
<212> TYPE: DNA
<213> ORGANISM: Artificial
<220> FEATURE:
<223> OTHER INFORMATION: Polynucleotide anti-CD100 VH CDR1

-continued

<210> SEQ ID NO 3
<211> LENGTH: 30
<212> TYPE: DNA
<213> ORGANISM: Artificial
<220> FEATURE:
<223> OTHER INFORMATION: Polynucleotide anti-CD100 VH CDR1

<400> SEQUENCE: 3
ggctacagct tcagcgacta ctacatgcac                                30

<210> SEQ ID NO 4
<211> LENGTH: 51
<212> TYPE: DNA
<213> ORGANISM: Artificial
<220> FEATURE:
<223> OTHER INFORMATION: Polynucleotide anti-CD100 VH CDR2

<400> SEQUENCE: 4
cagattaatc ctaccactgg cggcgctagc tacaaccaga agttcaaggg c         51

<210> SEQ ID NO 5
<211> LENGTH: 27
<212> TYPE: DNA
<213> ORGANISM: Artificial
<220> FEATURE:
<223> OTHER INFORMATION: Polynucleotide anti-CD100 VH CDR3

<400> SEQUENCE: 5
tattactacg gcagacactt cgatgtc                                   27

<210> SEQ ID NO 6
<211> LENGTH: 10
<212> TYPE: PRT
<213> ORGANISM: Artificial
<220> FEATURE:
<223> OTHER INFORMATION: Polypeptide anti-CD100 VH CDR1

<400> SEQUENCE: 6

Gly Tyr Ser Phe Ser Asp Tyr Tyr Met His
1               5                   10

<210> SEQ ID NO 7
<211> LENGTH: 17
<212> TYPE: PRT
<213> ORGANISM: Artificial
<220> FEATURE:
<223> OTHER INFORMATION: Polypeptide anti-CD100 VH CDR2

<400> SEQUENCE: 7

Gln Ile Asn Pro Thr Thr Gly Gly Ala Ser Tyr Asn Gln Lys Phe Lys
1               5                   10                  15

Gly

<210> SEQ ID NO 8
<211> LENGTH: 9
<212> TYPE: PRT
<213> ORGANISM: Artificial
<220> FEATURE:
<223> OTHER INFORMATION: Polypeptide anti-CD100 VH CDR3

<400> SEQUENCE: 8

Tyr Tyr Tyr Gly Arg His Phe Asp Val
1               5

<210> SEQ ID NO 9
<211> LENGTH: 118
<212> TYPE: PRT
<213> ORGANISM: Artificial
<220> FEATURE:
<223> OTHER INFORMATION: Polypeptide anti-CD100 VH 2503

<400> SEQUENCE: 9

-continued

Gln Val Gln Leu Val Gln Ser Gly Ala Glu Val Lys Pro Gly Ser
1               5                   10                  15

Ser Val Lys Val Ser Cys Lys Ala Ser Gly Tyr Ser Phe Ser Asp Tyr
            20                  25                  30

Tyr Met His Trp Val Arg Gln Ala Pro Gly Gln Gly Leu Glu Trp Met
        35                  40                  45

Gly Gln Ile Asn Pro Thr Thr Gly Gly Ala Ser Tyr Asn Gln Lys Phe
    50                  55                  60

Lys Gly Lys Ala Thr Ile Thr Val Asp Lys Ser Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Tyr Tyr Tyr Gly Arg His Phe Asp Val Trp Gly Gln Gly Thr
            100                 105                 110

Thr Val Thr Val Ser Ser
        115

<210> SEQ ID NO 10
<211> LENGTH: 118
<212> TYPE: PRT
<213> ORGANISM: Artificial
<220> FEATURE:
<223> OTHER INFORMATION: Polypeptide anti-CD100 VH 67

<400> SEQUENCE: 10

Gln Val Gln Leu Gln Gln Ser Gly Pro Glu Leu Val Lys Pro Gly Ala
1               5                   10                  15

Ser Val Lys Ile Ser Cys Lys Ala Ser Gly Tyr Ser Phe Ser Asp Tyr
            20                  25                  30

Tyr Met His Trp Val Lys Gln Ser Pro Glu Asn Ser Leu Glu Trp Ile
        35                  40                  45

Gly Gln Ile Asn Pro Thr Thr Gly Gly Ala Ser Tyr Asn Gln Lys Phe
    50                  55                  60

Lys Gly Lys Ala Thr Leu Thr Val Asp Lys Ser Ser Ser Thr Ala Tyr
65                  70                  75                  80

Met Gln Leu Lys Ser Leu Thr Ser Glu Glu Ser Ala Val Tyr Tyr Cys
                85                  90                  95

Thr Arg Tyr Tyr Tyr Gly Arg His Phe Asp Val Trp Gly Gln Gly Thr
            100                 105                 110

Thr Val Thr Val Ser Ser
        115

<210> SEQ ID NO 11
<211> LENGTH: 45
<212> TYPE: DNA
<213> ORGANISM: Artificial
<220> FEATURE:
<223> OTHER INFORMATION: Polynucleotide anti-CD100 VL CDR1

<400> SEQUENCE: 11
aaggccagcc aaagcgtgga ttatgatggc gatagctata tgaac      45

<210> SEQ ID NO 12
<211> LENGTH: 21
<212> TYPE: DNA
<213> ORGANISM: Artificial
<220> FEATURE:
<223> OTHER INFORMATION: Polynucleotide anti-CD100 VL CDR2

```
<400> SEQUENCE: 12
gctgcatcca atctggaaag c                                              21

<210> SEQ ID NO 13
<211> LENGTH: 27
<212> TYPE: DNA
<213> ORGANISM: Artificial
<220> FEATURE:
<223> OTHER INFORMATION: Polynucleotide anti-CD100 VL CDR3

<400> SEQUENCE: 13
cagcaaagca atgaggatcc ctacacc                                        27

<210> SEQ ID NO 14
<211> LENGTH: 15
<212> TYPE: PRT
<213> ORGANISM: Artificial
<220> FEATURE:
<223> OTHER INFORMATION: Polypeptide anti-CD100 VL CDR1

<400> SEQUENCE: 14

Lys Ala Ser Gln Ser Val Asp Tyr Asp Gly Asp Ser Tyr Met Asn
1               5                   10                  15

<210> SEQ ID NO 15
<211> LENGTH: 7
<212> TYPE: PRT
<213> ORGANISM: Artificial
<220> FEATURE:
<223> OTHER INFORMATION: Polypeptide anti-CD100 VL CDR2

<400> SEQUENCE: 15

Ala Ala Ser Asn Leu Glu Ser
1               5

<210> SEQ ID NO 16
<211> LENGTH: 9
<212> TYPE: PRT
<213> ORGANISM: Artificial
<220> FEATURE:
<223> OTHER INFORMATION: Polypeptide anti-CD100 VL CDR3

<400> SEQUENCE: 16

Gln Gln Ser Asn Glu Asp Pro Tyr Thr
1               5

<210> SEQ ID NO 17
<211> LENGTH: 111
<212> TYPE: PRT
<213> ORGANISM: Artificial
<220> FEATURE:
<223> OTHER INFORMATION: Polypeptide anti-CD100 VL 2503

<400> SEQUENCE: 17

Asp Ile Val Met Thr Gln Ser Pro Asp Ser Leu Ala Val Ser Leu Gly
1               5                   10                  15

Glu Arg Ala Thr Ile Asn Cys Lys Ala Ser Gln Ser Val Asp Tyr Asp
            20                  25                  30

Gly Asp Ser Tyr Met Asn Trp Tyr Gln Gln Lys Pro Gly Gln Pro Pro
        35                  40                  45

Lys Leu Leu Ile Tyr Ala Ala Ser Asn Leu Glu Ser Gly Val Pro Asp
    50                  55                  60

Arg Phe Ser Gly Ser Gly Ser Gly Thr Asp Phe Thr Leu Thr Ile Ser
65                  70                  75                  80
```

```
Ser Leu Gln Ala Glu Asp Val Ala Val Tyr Tyr Cys Gln Gln Ser Asn
                85                  90                  95

Glu Asp Pro Tyr Thr Phe Gly Gln Gly Thr Lys Leu Glu Ile Lys
            100                 105                 110

<210> SEQ ID NO 18
<211> LENGTH: 111
<212> TYPE: PRT
<213> ORGANISM: Artificial
<220> FEATURE:
<223> OTHER INFORMATION: Polypeptide anti-CD100 VL 67

<400> SEQUENCE: 18

Asp Ile Val Met Thr Gln Ser Pro Ala Ser Leu Ala Val Ser Leu Gly
1               5                   10                  15

Gln Arg Ala Thr Ile Ser Cys Lys Ala Ser Gln Ser Val Asp Tyr Asp
            20                  25                  30

Gly Asp Ser Tyr Met Asn Trp Tyr Gln Gln Lys Pro Gly Gln Pro Pro
        35                  40                  45

Lys Leu Leu Ile Tyr Ala Ala Ser Asn Leu Glu Ser Gly Ile Pro Ala
    50                  55                  60

Arg Phe Ser Gly Ser Gly Ser Gly Thr Asp Phe Thr Leu Asn Ile His
65                  70                  75                  80

Pro Val Glu Glu Glu Asp Ala Ala Thr Tyr Tyr Cys Gln Gln Ser Asn
                85                  90                  95

Glu Asp Pro Tyr Thr Phe Gly Gly Gly Thr Lys Leu Glu Ile Lys
            100                 105                 110

<210> SEQ ID NO 19
<211> LENGTH: 354
<212> TYPE: DNA
<213> ORGANISM: Artificial
<220> FEATURE:
<223> OTHER INFORMATION: Polynucleotide anti-CD100 VH 2503

<400> SEQUENCE: 19
caggtgcagc tggtgcagag cggcgctgag gtgaagaagc tggcagcag cgtgaaggtc      60 tcctgcaagg ctagcggcta cagcttcagc gactactaca tgcactgggt gagacaggcc     120
cctggccaag cctggagtg atgggccag attaatccta ccactggcgg cgctagctac      180
aaccagaagt tcaagggcaa ggccaccatt accgtggaca aaagcaccag cacagcctac    240
atggagctga gcagcctgag aagcgaggac accgccgtgt attactgtgc cagatattac    300
tacggcagac acttcgatgt ctggggccaa ggcaccacgg tcaccgtctc ttca           354

<210> SEQ ID NO 20
<211> LENGTH: 354
<212> TYPE: DNA
<213> ORGANISM: Artificial
<220> FEATURE:
<223> OTHER INFORMATION: Polynucleotide anti-CD100 VH 67

<400> SEQUENCE: 20
caggtccagc tgcagcagtc tggacctgag ctggtgaagc tggggcttc agtgaagata      60 tcctgcaagg cttctggtta ctcattcagt gactactaca tgcactgggt gaagcaaagt     120
cctgaaaata gtcttgagtg gattggacag attaatccta ccactggggg tgctagctac    180
aaccagaagt tcaagggcaa ggccacatta actgtagata atcctccag cacagcctac    240 atgcagctca agagcctgac atctgaagag tctgcagtct attactgtac aagatattac    300
```

```
tacggtagac acttcgatgt ctggggccaa gggaccacgg tcaccgtttc ctca        354
```

```
<210> SEQ ID NO 21
<211> LENGTH: 333
<212> TYPE: DNA
<213> ORGANISM: Artificial
<220> FEATURE:
<223> OTHER INFORMATION: Polynucleotide anti-CD100 VL 2503

<400> SEQUENCE: 21
gacatcgtga tgacccagag cccagacagc ctggctgtga gcctgggcga gagggccacc    60
atcaactgca aggccagcca aagcgtggat tatgatggcg atagctatat gaactggtac   120
cagcagaaac caggccagcc tcctaagctg ctgatttacg ctgcatccaa tctggaaagc   180
ggcgtgcctg acagattcag cggcagcggc agcggcacag atttcactct gaccatcagc   240
agcctgcagg ctgaagatgt ggcagtgtat tactgtcagc aaagcaatga ggatccctac   300
accttcggcc aagggaccaa gctcgagatc aaa                                333
```

```
<210> SEQ ID NO 22
<211> LENGTH: 333
<212> TYPE: DNA
<213> ORGANISM: Artificial
<220> FEATURE:
<223> OTHER INFORMATION: Polynucleotide anti-CD100 VL 67

<400> SEQUENCE: 22
gacattgtga tgacccagtc tccagcttct ttggctgtgt ctctagggca gagggccacc    60
atctcctgca aggccagcca agtgttgat tatgatggtg atagttatat gaactggtac    120
caacagaaac caggacagcc acccaaactc ctcatctatg ctgcatccaa tctagaatct   180
gggatcccag ccaggtttag tggcagtggg tctgggacag acttcaccct caacatccat   240
cctgtggagg aggaggatgc tgcaacctat tactgtcagc aaagtaatga ggatccgtac   300
acgttcggag gggggaccaa gctcgagatc aaa                                333
```

```
<210> SEQ ID NO 23
<211> LENGTH: 2586
<212> TYPE: DNA
<213> ORGANISM: Homo sapiens

<400> SEQUENCE: 23
atgaggatgt gcacccccat tagggggctg ctcatggccc ttgcagtgat gtttgggaca    60
gcgatggcat ttgcacccat accccggatc acctgggagc acagagaggt gcacctggtg   120
cagtttcatg agccagacat ctacaactac tcagccttgc tgctgagcga ggacaaggac   180
accttgtaca taggtgcccg ggaggcggtc ttcgctgtga acgcactcaa catctccgag   240
aagcagcatg aggtgtattg gaaggtctca gaagacaaaa agcaaaatg tgcagaaaag   300 gggaaatcaa acagacaga gtgcctcaac tacatccggg tgctgcagcc actcagcgcc   360
acttcccttt acgtgtgtgg gaccaacgca ttccagccgg cctgtgacca cctgaactta   420
acatccttta gtttctggg gaaaaatgaa gatggcaaag aagatgtcc ctttgaccca   480 gcacacagct acacatccgt catggttgat ggagaacttt attcggggac gtcgtataat   540 ttttgggaa gtgaacccat catctcccga aattcttccc acagtcctct gaggacagaa   600
tatgcaatcc cttggctgaa cgagcctagt ttcgtgtttg ctgacgtgat ccgaaaaagc   660
ccagacagcc ccgacggcga ggatgacagg gtctacttct tcttcacgga ggtgtctgtg   720
```

```
gagtatgagt ttgtgttcag ggtgctgatc ccacggatag caagagtgtg caaggggggac    780
cagggcggcc tgaggacctt gcagaagaaa tggacctcct tcctgaaagc ccgactcatc    840
tgctcccggc cagacagcgg cttggtcttc aatgtgctgc gggatgtctt cgtgctcagg    900
tccccgggcc tgaaggtgcc tgtgttctat gcactcttca ccccacagct gaacaacgtg    960
gggctgtcgg cagtgtgcgc ctacaacctg tccacagccg aggaggtctt ctcccacggg   1020
aagtacatgc agagcaccac agtggagcag tcccacacca gtgggtgcg ctataatggc    1080
ccggtaccca agccgcggcc tggagcgtgc atcgacagcg aggcacgggc cgccaactac   1140
accagctcct tgaatttgcc agacaagacg ctgcagttcg ttaaagacca ccctttgatg   1200
gatgactcgg taaccccaat agacaacagg cccaggttaa tcaagaaaga tgtgaactac   1260
acccagatcg tggtggaccg gacccaggcc ctggatggga ctgtctatga tgtcatgttt   1320
gtcagcacag accggggagc tctgcacaaa gccatcagcc tcgagcacgc tgttcacatc   1380
atcgaggaga cccagctctt ccaggacttt gagccagtcc agaccctgct gctgtcttca   1440
aagaagggca acaggtttgt ctatgctggc tctaactcgg gcgtggtcca ggccccgctg   1500
gccttctgtg ggaagcacgg cacctgcgag gactgtgtgc tggcgcggga cccctactgc   1560
gcctggagcc cgcccacagc gacctgcgtg gctctgcacc agaccgagag ccccagcagg   1620
ggtttgattc aggagatgag cggcgatgct tctgtgtgcc cggataaaag taaaggaagt   1680
taccggcagc atttttttcaa gcacggtggc acagcggaac tgaaatgctc ccaaaaatcc   1740
aacctggccc gggtcttttg gaagttccag aatggcgtgt tgaaggccga gagccccaag   1800
tacggtctta tgggcagaaa aaacttgctc atcttcaact tgtcagaagg agacagtggg   1860
gtgtaccagt gcctgtcaga ggagagggtt aagaacaaaa cggtcttcca agtggtcgcc   1920
aagcacgtcc tggaagtgaa ggtggttcca agcccgtag tggcccccac cttgtcagtt   1980
gttcagacag aaggtagtag gattgccacc aaagtgttgg tggcatccac ccaagggtct   2040
tctcccccaa ccccagccgt gcaggccacc tcctccgggg ccatcaccct tcctcccaag   2100
cctgcgccca ccggcacatc ctgcgaacca agatcgtca tcaacacggt ccccccagctc   2160
cactcggaga aaaccatgta tcttaagtcc agcgacaacc gcctcctcat gtccctcttc   2220
ctcttcttct ttgttctctt cctctgcctc tttttctaca actgctataa gggataccg    2280
cccagacagt gcttgaaatt ccgctcggcc ctactaattg ggaagaagaa gcccaagtca   2340
gatttctgtg accgtgagca gagcctgaag gagacgttag tagagccagg gagcttctcc   2400
cagcagaatg gggagcaccc caagccagcc ctggacaccg gctatgagac cgagcaagac   2460
accatcacca gcaaagtccc cacggatagg gaggactcac agaggatcga cgacctttct   2520
gccagggaca gccctttga cgtcaagtgt gagctgaagt tcgctgactc agacgcagat   2580
ggagac                                                              2586
```

```
<210> SEQ ID NO 24
<211> LENGTH: 13
<212> TYPE: PRT
<213> ORGANISM: Artificial
<220> FEATURE:
<223> OTHER INFORMATION: Peptide epitope of proteolipid protein
      PLP(139-151)

<400> SEQUENCE: 24

His Ser Leu Gly Lys Trp Leu Gly His Pro Asp Lys Phe
1               5                   10
```

```
<210> SEQ ID NO 25
<211> LENGTH: 118
<212> TYPE: PRT
<213> ORGANISM: Artificial
<220> FEATURE:
<223> OTHER INFORMATION: Polypeptide anti-CD100 VH 76

<400> SEQUENCE: 25

Gln Val Gln Leu Gln Gln Ser Gly Ala Glu Leu Ala Lys Pro Gly Ala
1               5                   10                  15

Ser Val Lys Met Ser Cys Lys Ala Ser Gly Tyr Thr Phe Thr Arg Tyr
            20                  25                  30

Trp Met His Trp Val Lys Gln Arg Pro Gly Gln Gly Leu Glu Trp Ile
        35                  40                  45

Gly Tyr Ile Asn Pro Ser Thr Gly Tyr Ser Asp Tyr Asn Gln Lys Phe
    50                  55                  60

Lys Asp Lys Ala Thr Leu Thr Ala Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Asp Pro Tyr Gly Trp Thr Met Asp Ser Trp Gly Gln Gly Thr
            100                 105                 110

Leu Val Thr Val Ser Ser
        115

<210> SEQ ID NO 26
<211> LENGTH: 10
<212> TYPE: PRT
<213> ORGANISM: Artificial
<220> FEATURE:
<223> OTHER INFORMATION: Polypeptide anti-CD100 VH 76 CDR1

<400> SEQUENCE: 26

Gly Tyr Thr Phe Thr Arg Tyr Trp Met His
1               5                   10

<210> SEQ ID NO 27
<211> LENGTH: 17
<212> TYPE: PRT
<213> ORGANISM: Artificial
<220> FEATURE:
<223> OTHER INFORMATION: Polypeptide anti-CD100 VH 76 CDR2

<400> SEQUENCE: 27

Tyr Ile Asn Pro Ser Thr Gly Tyr Ser Asp Tyr Asn Gln Lys Phe Lys
1               5                   10                  15

Asp

<210> SEQ ID NO 28
<211> LENGTH: 9
<212> TYPE: PRT
<213> ORGANISM: Artificial
<220> FEATURE:
<223> OTHER INFORMATION: Polypeptide anti-CD100 VH 76 CDR3

<400> SEQUENCE: 28

Asp Pro Tyr Gly Trp Thr Met Asp Ser
1               5

<210> SEQ ID NO 29
<211> LENGTH: 107
<212> TYPE: PRT
<213> ORGANISM: Artificial
```

-continued

<220> FEATURE:
<223> OTHER INFORMATION: Polypeptide anti-CD100 VL 76

<400> SEQUENCE: 29

Asp Ile Gln Met Thr Gln Ser Pro Ser Ser Leu Ser Ala Ser Leu Gly
1               5                   10                  15

Asp Thr Ile Thr Ile Thr Cys His Ala Ser Gln Asn Ile Asn Val Trp
            20                  25                  30

Leu Ser Trp Tyr Gln Gln Lys Pro Gly Asn Ile Pro Lys Leu Leu Ile
        35                  40                  45

Tyr Lys Ala Ser Asn Leu His Thr Gly Val Pro Ser Arg Phe Ser Gly
    50                  55                  60

Ser Gly Ser Gly Thr Gly Phe Thr Leu Thr Ile Ser Ser Leu Gln Pro
65                  70                  75                  80

Glu Asp Ile Ala Thr Tyr Tyr Cys Gln Gln Gly Gln Ser Tyr Pro Tyr
                85                  90                  95

Thr Phe Gly Gly Gly Thr Lys Leu Glu Ile Lys
            100                 105

<210> SEQ ID NO 30
<211> LENGTH: 11
<212> TYPE: PRT
<213> ORGANISM: Artificial
<220> FEATURE:
<223> OTHER INFORMATION: Polypeptide anti-CD100 VL 76 CDR1

<400> SEQUENCE: 30

His Ala Ser Gln Asn Ile Asn Val Trp Leu Ser
1               5                   10

<210> SEQ ID NO 31
<211> LENGTH: 7
<212> TYPE: PRT
<213> ORGANISM: Artificial
<220> FEATURE:
<223> OTHER INFORMATION: Polypeptide anti-CD100 VL 76 CDR2

<400> SEQUENCE: 31

Lys Ala Ser Asn Leu His Thr
1               5

<210> SEQ ID NO 32
<211> LENGTH: 9
<212> TYPE: PRT
<213> ORGANISM: Artificial
<220> FEATURE:
<223> OTHER INFORMATION: Polypeptide anti-CD100 VL 76 CDR3

<400> SEQUENCE: 32

Gln Gln Gly Gln Ser Tyr Pro Tyr Thr
1               5

<210> SEQ ID NO 33
<211> LENGTH: 354
<212> TYPE: DNA
<213> ORGANISM: Artificial
<220> FEATURE:
<223> OTHER INFORMATION: Polynucleotide anti-CD100 VH 76

<400> SEQUENCE: 33
caggtccagc tgcagcagtc tggggctgaa ctggcaaaac ctggggcctc agtgaagatg     60
tcctgcaagg cttctggcta cacctttact aggtactgga tgcactgggt aaaacagagg    120

```
cctggacagg gtctggaatg gattggatac attaatccta gcactggtta ttctgattac    180
aatcagaagt tcaaggacaa ggccacattg actgcagaca atcctccag cacagcctac    240 atgcaactga gcagcctgac atctgaggac tctgcagtct attactgtgc aagagacccc    300
tacggctgga ctatggactc ctggggccaa gggactctgg tcaccgtctc ctca          354
```

<210> SEQ ID NO 34
<211> LENGTH: 30
<212> TYPE: DNA
<213> ORGANISM: Artificial
<220> FEATURE:
<223> OTHER INFORMATION: Polynucleotide anti-CD100 VH 76 CDR1

<400> SEQUENCE: 34

```
ggctacacct ttactaggta ctggatgcac                                      30
```

<210> SEQ ID NO 35
<211> LENGTH: 51
<212> TYPE: DNA
<213> ORGANISM: Artificial
<220> FEATURE:
<223> OTHER INFORMATION: Polynucleotide anti-CD100 VH 76 CDR2

<400> SEQUENCE: 35

```
tacattaatc ctagcactgg ttattctgat tacaatcaga agttcaagga c              51
```

<210> SEQ ID NO 36
<211> LENGTH: 27
<212> TYPE: DNA
<213> ORGANISM: Artificial
<220> FEATURE:
<223> OTHER INFORMATION: Polynucleotide anti-CD100 VH 76 CDR3

<400> SEQUENCE: 36

```
gaccccctacg gctggactat ggactcc                                        27
```

<210> SEQ ID NO 37
<211> LENGTH: 321
<212> TYPE: DNA
<213> ORGANISM: Artificial
<220> FEATURE:
<223> OTHER INFORMATION: Polynucleotide anti-CD100 VL 76

<400> SEQUENCE: 37

```
gacatccaga tgacccagtc tccatccagt ctgtctgcat cccttggaga cacaattacc    60
atcacttgcc atgccagtca gaacattaat gtttggttaa gctggtacca gcagaaacca    120
ggaaatattc ctaaactatt gatctataag gcttccaact tgcacacagg cgtcccatca    180
aggtttagtg gcagtggatc tggaacaggt ttcacattaa ccatcagcag cctgcagcct    240
gaagacattg ccacttacta ctgtcaacag ggtcaaagtt atccgtacac gttcggaggg    300
gggaccaagc tcgagatcaa a                                               321
```

<210> SEQ ID NO 38
<211> LENGTH: 33
<212> TYPE: DNA
<213> ORGANISM: Artificial
<220> FEATURE:
<223> OTHER INFORMATION: Polynucleotide anti-CD100 VL 76 CDR1

<400> SEQUENCE: 38

```
catgccagtc agaacattaa tgtttggtta agc                                  33
```

```
<210> SEQ ID NO 39
<211> LENGTH: 21
<212> TYPE: DNA
<213> ORGANISM: Artificial
<220> FEATURE:
<223> OTHER INFORMATION: Polynucleotide anti-CD100 VL 76 CDR2

<400> SEQUENCE: 39
aaggcttcca acttgcacac a                                          21

<210> SEQ ID NO 40
<211> LENGTH: 27
<212> TYPE: DNA
<213> ORGANISM: Artificial
<220> FEATURE:
<223> OTHER INFORMATION: Polynucleotide anti-CD100 VL 76 CDR3

<400> SEQUENCE: 40
caacagggtc aaagttatcc gtacacg                                    27

<210> SEQ ID NO 41
<211> LENGTH: 123
<212> TYPE: PRT
<213> ORGANISM: Artificial Sequence
<220> FEATURE:
<223> OTHER INFORMATION: H7230 Heavy chain variable region

<400> SEQUENCE: 41

Gln Val Gln Leu Val Gln Ser Gly Ala Glu Leu Arg Lys Pro Gly Ala
1               5                   10                  15

Ser Val Lys Ile Ser Cys Lys Ala Ser Gly Tyr Ser Leu Thr Tyr Tyr
            20                  25                  30

Gly Met Asn Trp Val Arg Gln Ala Pro Gly Gln Gly Leu Glu Trp Met
        35                  40                  45

Gly Trp Ile Asn Thr Phe Thr Gly Asp Ser Thr Tyr Ala Gln Asp Phe
    50                  55                  60

Thr Gly Arg Phe Val Phe Ser Leu Asp Thr Ser Val Ser Thr Ala Tyr
65                  70                  75                  80

Leu Gln Ile Ser Ser Leu Lys Ala Glu Asp Met Ala Met Tyr Tyr Cys
                85                  90                  95

Ala Lys Tyr Pro His Tyr Tyr Gly Ser Ser His Trp Tyr Phe Asp Val
            100                 105                 110

Trp Gly Gln Gly Thr Thr Val Thr Val Ser Ser
        115                 120

<210> SEQ ID NO 42
<211> LENGTH: 107
<212> TYPE: PRT
<213> ORGANISM: Artificial Sequence
<220> FEATURE:
<223> OTHER INFORMATION: L7104 Light Chain variable region

<400> SEQUENCE: 42

Glu Ile Val Leu Thr Gln Ser Pro Ala Thr Leu Ser Val Ser Pro Gly
1               5                   10                  15

Glu Arg Ala Thr Leu Ser Cys Arg Ala Ser Gln Ser Val Asn Ser Asn
            20                  25                  30

Leu Ala Trp Tyr Gln Gln Lys Pro Gly Gln Ala Pro Arg Val Leu Ile
        35                  40                  45

Tyr Gly Ala Ser Thr Arg Ala Thr Gly Ile Pro Ala Arg Phe Ser Gly
    50                  55                  60
```

```
Ser Gly Ser Gly Thr Glu Phe Thr Leu Thr Ile Ser Ser Leu Gln Ser
 65                  70                  75                  80

Glu Asp Phe Ala Val Tyr Tyr Cys Gln Gln Tyr Ser Asp Ile Pro Trp
                 85                  90                  95

Thr Phe Gly Gln Gly Thr Lys Leu Glu Ile Lys
            100                 105

<210> SEQ ID NO 43
<211> LENGTH: 10
<212> TYPE: PRT
<213> ORGANISM: Artificial Sequence
<220> FEATURE:
<223> OTHER INFORMATION: H7230 VH-CDR1

<400> SEQUENCE: 43

Gly Tyr Ser Leu Thr Tyr Tyr Gly Met Asn
1               5                   10

<210> SEQ ID NO 44
<211> LENGTH: 17
<212> TYPE: PRT
<213> ORGANISM: Artificial Sequence
<220> FEATURE:
<223> OTHER INFORMATION: H7230 VH-CDR2

<400> SEQUENCE: 44

Trp Ile Asn Thr Phe Thr Gly Asp Ser Thr Tyr Ala Gln Asp Phe Thr
1               5                   10                  15

Gly

<210> SEQ ID NO 45
<211> LENGTH: 14
<212> TYPE: PRT
<213> ORGANISM: Mus musculus

<400> SEQUENCE: 45

Tyr Pro His Tyr Tyr Gly Ser Ser His Trp Tyr Phe Asp Val
1               5                   10

<210> SEQ ID NO 46
<211> LENGTH: 11
<212> TYPE: PRT
<213> ORGANISM: Artificial Sequence
<220> FEATURE:
<223> OTHER INFORMATION: L7104 VL-CDR1

<400> SEQUENCE: 46

Arg Ala Ser Gln Ser Val Asn Ser Asn Leu Ala
1               5                   10

<210> SEQ ID NO 47
<211> LENGTH: 7
<212> TYPE: PRT
<213> ORGANISM: Artificial Sequence
<220> FEATURE:
<223> OTHER INFORMATION: L7104 VL-CDR2

<400> SEQUENCE: 47

Gly Ala Ser Thr Arg Ala Thr
1               5

<210> SEQ ID NO 48
<211> LENGTH: 9
<212> TYPE: PRT
<213> ORGANISM: Artificial Sequence
```

<220> FEATURE:
<223> OTHER INFORMATION: L7104 VL-CDR3

<400> SEQUENCE: 48

Gln Gln Tyr Ser Asp Ile Pro Trp Thr
1               5

<210> SEQ ID NO 49
<211> LENGTH: 369
<212> TYPE: DNA
<213> ORGANISM: Artificial Sequence
<220> FEATURE:
<223> OTHER INFORMATION: H7230 Heavy chain variable region

<400> SEQUENCE: 49

```
caggtgcagc tggtgcagtc tggggctgaa ttgaggaagc ctggggcctc agtgaaaatt      60
tcctgcaagg cttctggata cagcttgaca tactatggta tgaattgggt gcgacaggcc     120
cccggacaag ggcttgagtg gatgggatgg atcaacacct tcactgggga ctcaacgtat     180
gcccaggact tcacaggacg gtttgtcttc tccttgacaa cctctgtcag cacggcatat     240
ctgcagatca gcagcctaaa ggctgaggac atggccatgt attactgcgc caagtaccct     300
cactactacg gcagcagcca ctggtacttc gacgtgtggg gccagggcac cacggtcacc     360
gtctcctca                                                             369
```

<210> SEQ ID NO 50
<211> LENGTH: 321
<212> TYPE: DNA
<213> ORGANISM: Artificial Sequence
<220> FEATURE:
<223> OTHER INFORMATION: L7104 Light chain variable region

<400> SEQUENCE: 50

```
gaaattgtgt tgacgcagtc tccagccacc ctgtctgtgt ctccagggga aagagccacc      60
ctctcctgca gggccagtca gagtgttaac agcaacttag cctggtacca gcagaaacct     120
ggccaggctc ccagggtcct catctatggt gcttccacca gggccactgg catcccagcc     180
aggttcagtg gcagtgggtc tgggacagag ttcactctca ccatcagcag cctgcagtct     240
gaggattttg cagtttatta ctgtcagcaa tatagtgata tcccgtggac gttcggccag     300
gggaccaaac tcgagatcaa a                                                321
```

<210> SEQ ID NO 51
<211> LENGTH: 30
<212> TYPE: DNA
<213> ORGANISM: Artificial Sequence
<220> FEATURE:
<223> OTHER INFORMATION: H7230 VH-CDR1

<400> SEQUENCE: 51

```
ggatacagct tgacatacta tggtatgaat                                        30
```

<210> SEQ ID NO 52
<211> LENGTH: 51
<212> TYPE: DNA
<213> ORGANISM: Artificial Sequence
<220> FEATURE:
<223> OTHER INFORMATION: H7230 VH-CDR2

<400> SEQUENCE: 52

```
tggatcaaca ccttcactgg ggactcaacg tatgcccagg acttcacagg a                51
```

```
<210> SEQ ID NO 53
<211> LENGTH: 42
<212> TYPE: DNA
<213> ORGANISM: Artificial Sequence
<220> FEATURE:
<223> OTHER INFORMATION: H7230 VH-CDR3

<400> SEQUENCE: 53
taccctcact actacggcag cagccactgg tacttcgacg tg                          42

<210> SEQ ID NO 54
<211> LENGTH: 33
<212> TYPE: DNA
<213> ORGANISM: Artificial Sequence
<220> FEATURE:
<223> OTHER INFORMATION: L7104 VL-CDR1

<400> SEQUENCE: 54
agggccagtc agagtgttaa cagcaactta gcc                                    33

<210> SEQ ID NO 55
<211> LENGTH: 21
<212> TYPE: DNA
<213> ORGANISM: Artificial Sequence
<220> FEATURE:
<223> OTHER INFORMATION: L7104 VL-CDR2

<400> SEQUENCE: 55
ggtgcttcca ccagggccac t                                                 21

<210> SEQ ID NO 56
<211> LENGTH: 27
<212> TYPE: DNA
<213> ORGANISM: Artificial Sequence
<220> FEATURE:
<223> OTHER INFORMATION: L7104 VL-CDR3

<400> SEQUENCE: 56
cagcaatata gtgatatccc gtggacg                                           27
```

USE OF THE COMBINATION OF SEMAPHORIN-4D INHIBITORY MOLECULES AND VEGF INHIBITORY MOLECULES TO INHIBIT ANGIOGENESIS

CROSS-REFERENCE TO RELATED APPLICATIONS

This application claims priority benefit to U.S. Provisional Appl. No. 61/567,531, filed on Dec. 6, 2011 and U.S. Provisional Appl. No. 61/576,188, filed on Dec. 15, 2011, the contents of each are hereby incorporated by reference in their entirety.

REFERENCE TO SEQUENCE LISTING SUBMITTED ELECTRONICALLY

The content of the electronically submitted sequence listing in ASCII text file (Name: SequenceID_Listing.ascii.txt; Size: 39,779 bytes; and Date of Creation: Nov. 30, 2012) filed with the application is incorporated herein by reference in its entirety.

BACKGROUND OF THE INVENTION

Semaphorin 4D (SEMA4D), also known as CD100, is a transmembrane protein (e.g., SEQ ID NO: 1 (human); SEQ ID NO: 2 (murine)) that belongs to the semaphorin gene family. SEMA4D is expressed on the cell surface as a homodimer, but upon cell activation SEMA4D can be released from the cell surface via proteolytic cleavage to generate sSEMA4D, a soluble form of the protein, which is also biologically active. See Suzuki et al., *Nature Rev. Immunol.* 3:159-167 (2003); Kikutani et al., *Nature Immunol.* 9:17-23 (2008).

Immunohistochemical analysis of SEMA4D in a large tumor sample collection revealed that SEMA4D overexpression is a very frequent event in head and neck, prostate, ovarian, pancreatic, colon, breast, and lung cancers as well as being significantly expressed in other tumor types. SEMA4D is a potent pro-angiogenic molecule. Activation through a SEMA4D receptor, Plexin-B1 promotes angiogenesis both in vitro and in vivo. See, e.g., Sierra JR, et al. *J Exp Med* 205:1673-1685 (2008). Plexin-B1 is referred to herein and in the scientific literature interchangeably as, Plexin-B1, plexin-B1, Plexin B1 or plexin B1.

The angiogenic response elicited by SEMA4D is comparable to that elicited by other angiogenic molecules, such as vascular endothelial growth factor (VEGF). It is well established that VEGF and its receptors are key regulators of new blood vessel formation, or angiogenesis. The VEGF gene family has several members, including VEGF-A (also referred to herein as "VEGF"), VEGF-B, VEGF-C, VEGF-D, VEGF-E, and P1GF. See, Ho and Kuo, Int. *J. Biochem Cell Biol.* 2007; 39(7-8): 1349-1357. There are numerous alternatively spliced isoforms of human VEGF, including $VEGF_{165}$, $VEGF_{121}$, $VEGF_{189}$, and $VEGF_{206}$. See Ho and Kuo, *Int. J. Biochem Cell Biol.* 2007; 39(7-8): 1349-1357; Ferrara et al., *Nature Med.* 2003; 9 (6):669-676. The $VEGF_{165}$ isoform is the most prevalent and mitogenic and is most similar in properties to the 45 kDa native VEGF. See Ho and Kuo, *Int. J. Biochem Cell Biol.* 2007; 39(7-8): 1349-1357; Ferrara et al., *Nature Med.* 2003; 9 (6):669-676.

VEGF exists as a 45 kD homodimeric glycoprotein which binds to two related tyrosine kinase receptors. Ferrara et al., *Nature Med.* 2003; 9 (6):669-676. VEGFR-1 (also known as Flt-1), is a high affinity receptor for VEGF whose function is not fully understood. VEGFR-2 (also known as KDR or Flk1), is the other high affinity receptor for VEGF, and is the receptor through which the pro-angiogeneic activity of VEGF is believed to be induced. See Ferrara et al., *Nature Med.* 2003; 9 (6):669-676. VEGFR-2 forms a dimer and autophosphorylates when bound to VEGF. Dougher and Terman, *Oncogene.* 1999; 18: 1619-1627. This, in turn, activates several signaling cascades that promote endothelial cell growth and migration, and which, ultimately, lead to angiogenesis. See Hicklin and Ellis, *J. Clin. Oncol.* 2005; 23(5): 1011-1027.

During embryonic and postnatal development, VEGF participates in angiogenesis, vasculogenesis, and lymphangiogenesis. VEGF has also been found to play a role in adult processes, as well, including ovarian angiogenesis, endochondral bone formation, tissue regeneration, survival of hematopoietic stem cells, and regulation of erythropoietin. See, Ho and Kuo, *Int. J. Biochem Cell Biol.* 2007; 39(7-8): 1349-1357. It is the involvement of VEGF in disease processes such as cancer and other neoplastic conditions, inflammatory disease, ocular disease, and ischemic disease that makes it a potential target for treatment.

Angiogenesis is a requirement for a tumor to grow beyond 1 to 2 mm. The formation of new vasculature is a result of the tumor environment "switching" on several pathways that promote tumor angiogenesis. Inhibition of VEGF-induced angiogenesis by a monoclonal antibody that specifically binds to VEGF was shown to suppress tumor growth in vivo. See Kim et al., *Nature* 1993; 362: 841-844. This observation was the motivation for development of a therapeutic antibody, bevacizumab, to neutralize VEGF and slow the progression of cancer.

There is significant toxicity associated with clinical use of ant-VEGF antibodies. There remains, therefore, a need for cancer treatments, and in particular therapeutics that inhibit, suppress, prevent, slow the progression of, shrink, or directly attack angiogenesis.

BRIEF SUMMARY OF THE INVENTION

Methods for inhibiting tumor angiogenesis in a cancer patient are disclosed herein. According to aspects of the invention illustrated herein, the method included administering to the subject an effective amount of a first isolated binding molecule which specifically binds to semaphorin-4D (SEMA4D) and an effective amount of a second isolated binding molecule which specifically binds to VEGF.

According to aspects illustrated herein, there is provided a method of treating cancer in a subject, including administering to the subject an effective amount of a first isolated binding molecule which specifically binds to semaphorin-4D (SEMA4D) and an effective amount of a second isolated binding molecule which specifically binds to VEGF, wherein the first isolated binding molecule and second isolated binding molecule act to inhibit angiogenesis.

According to aspects illustrated herein, there is provided a method for inhibiting angiogenesis in a subject, including administering to the subject an effective amount of a first isolated binding molecule which inhibits interaction of semaphorin-4D (SEMA4D) with Plexin-B1 and an effective amount of a second isolated binding molecule which inhibits interaction of VEGF with VEGFR2.

BRIEF DESCRIPTION OF THE DRAWINGS/FIGURES

FIG. 1: Measurement of tumor volume in tumor grafted mice showing mean tumor volume among the four treatment groups (IgG Control; VX15/2503 antibody; anti-VEGF antibody, and VX15/2503 antibody+anti-VEGF antibody). "anti-VEGF antibody" is Mouse IgG2A MAb 2931.

Figure 2:
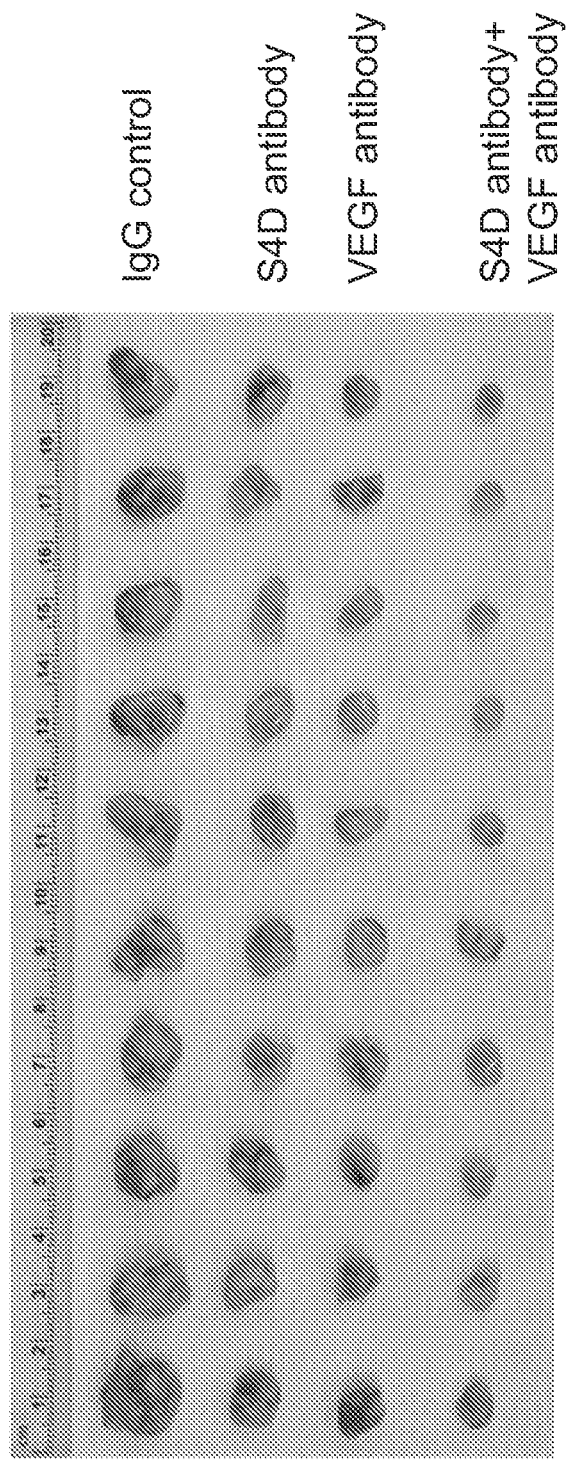

FIG. 2: Photograph of the extracted tumors from mice among the four treatment groups (IgG Control; VX15/2503 antibody; anti-VEGF antibody, and VX15/2503 antibody+anti-VEGF antibody). "S4D antibody" is VX15/2503. "VEGF antibody" is Mouse IgG2A MAb 2931.

Figure 3:
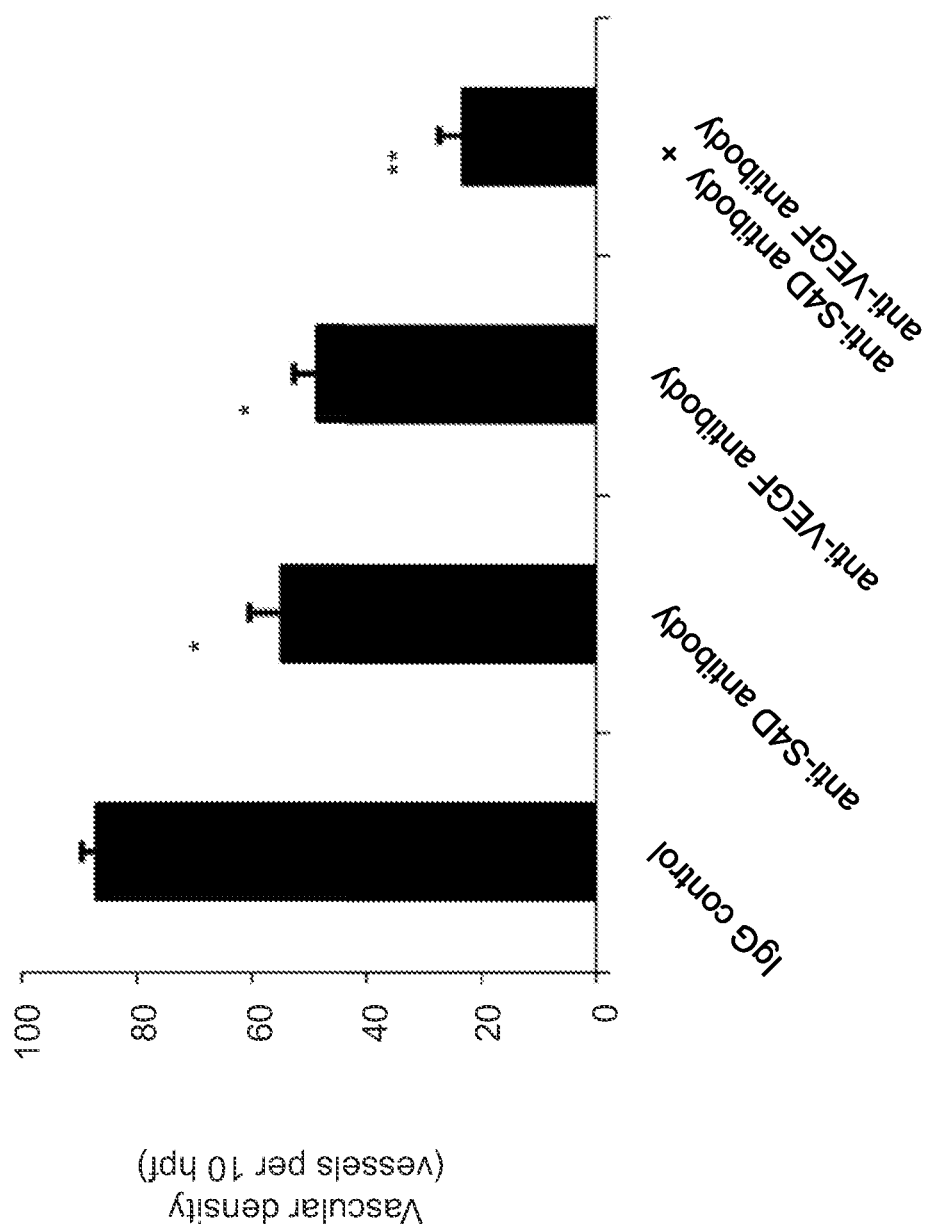

FIG. 3: Measurement of vascular density in tumor grafted mice among the four treatment groups (IgG Control; VX15/2503 antibody; anti-VEGF antibody, and VX15/2503 antibody+anti-VEGF antibody). "Anti-S4D antibody" is VX15/2503. "Anti-VEGF antibody" is Mouse IgG2A MAb 2931.

DETAILED DESCRIPTION OF THE INVENTION

I. Definitions

It is to be noted that the term "a" or "an" entity refers to one or more of that entity; for example, "an anti-SEMA4D antibody" is understood to represent one or more anti-SEMA4D antibodies. As such, the terms "a" (or "an"), "one or more," and "at least one" can be used interchangeably herein.

As used herein, the terms "cancer" and "cancerous" refer to or describe the physiological condition in mammals in which a population of cells are characterized by unregulated cell growth. Examples of cancer include, but are not limited to, carcinoma, lymphoma, blastoma, sarcoma, and leukemia. More particular examples of such cancers include squamous cell cancer, small-cell lung cancer, non-small cell lung cancer, adenocarcinoma of the lung, squamous carcinoma of the lung, cancer of the peritoneum, hepatocellular cancer, gastrointestinal cancer, gastric, pancreatic cancer, glioblastoma, cervical cancer, ovarian cancer, liver cancer, bladder cancer, brain cancer, hepatoma, breast cancer, colon cancer, colorectal cancer, endometrial or uterine carcinoma, esophageal cancer, salivary gland carcinoma, sarcoma, kidney cancer, liver cancer, prostate cancer, vulval cancer, thyroid cancer, hepatic carcinoma and various types of head and neck cancers.

"Invasive angiogenesis" refers to the formation of blood vessels for the support of pathological conditions, including malignant and non-malignant tumors as well as the abnormal formation of new blood vessels in macular degeneration.

The terms "proliferative disorder" and "proliferative disease" refer to disorders associated with abnormal cell proliferation such as cancer.

"Tumor" and "neoplasm" as used herein refer to any mass of tissue that result from excessive cell growth or proliferation, either benign (noncancerous) or malignant (cancerous) including pre-cancerous lesions. In certain embodiments, tumors described herein express Plexin-B1, and can express SEMA4B and activated Met.

The term "therapeutically effective amount" refers to an amount of an antibody, polypeptide, polynucleotide, small organic molecule, or other drug effective to "treat" a disease or disorder in a subject or mammal. In the case of cancer, the therapeutically effective amount of the drug can reduce the number of cancer cells; retard or stop cancer cell division, reduce or retard an increase in tumor size; inhibit, e.g., suppress, retard, prevent, shrink, stop, or reverse tumor angiogenesis; inhibit, e.g., suppress, retard, prevent, stop, or reverse the formation of new blood vessels; relieve to some extent one or more of the symptoms associated with the cancer, reduce morbidity and mortality; improve quality of life; or a combination of such effects. To the extent the drug prevents growth and/or kills existing cancer cells, it can be referred to as cytostatic and/or cytotoxic.

Terms such as "treating" or "treatment" or "to treat" or "alleviating" or "to alleviate" refer to both 1) therapeutic measures that cure, slow down, lessen symptoms of, reverse, and/or halt progression of a diagnosed pathologic condition or disorder and 2) prophylactic or preventative measures that prevent and/or slow the development of a targeted pathologic condition or disorder. Thus those in need of treatment include those already with the disorder; those prone to have the disorder; and those in whom the disorder is to be prevented. A subject is successfully "treated" according to the methods of the present invention if the patient shows one or more of the following: a reduction in the number of blood vessels; a reduction in the tumor size; or retardation or reversal of tumor growth; inhibition, e.g., suppression, prevention, retardation, shrinkage, or reversal of angiogenesis, i.e., of formation of new blood vessels; inhibition of, e.g., suppression of, retardation of, prevention of, shrinkage of, reversal of or an absence of tumor growth; relief of one or more symptoms associated with the specific cancer; reduced morbidity and mortality; improvement in quality of life; or some combination of effects. Beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already with the condition or disorder as well as those prone to have the condition or disorder or those in which the condition or disorder is to be prevented.

By "subject" or "individual" or "animal" or "patient" or "mammal," is meant any subject, particularly a mammalian subject, for whom diagnosis, prognosis, or therapy is desired. Mammalian subjects include humans, domestic animals, farm animals, and zoo, sports, or pet animals such as dogs, cats, guinea pigs, rabbits, rats, mice, horses, cattle, cows, bears, and so on.

As used herein, phrases such as "a subject that would benefit from administration of an anti-SEMA4D antibody and/or an anti-VEGF antibody" and "an animal in need of treatment" includes subjects, such as mammalian subjects, that would benefit from administration of an anti-SEMA4D antibody and an anti-VEGF antibody and/or from treatment.

A "binding molecule" or "antigen binding molecule" of the present invention refers in its broadest sense to a molecule that specifically binds an antigenic determinant. In one embodiment, the binding molecule specifically binds to SEMA4D, e.g., a transmembrane SEMA4D polypeptide of about 150 kDa or a soluble SEMA4D polypeptide of about 120 kDa (commonly referred to as sSEMA4D). In another embodiment, the binding molecule specifically binds to native VEGF ("VEGF-A"), e.g., a 45 kDa homodimeric glycoprotein, or other allelic or variant forms of VEGF. In another embodiment, a binding molecule of the invention is an antibody or an antigen binding fragment thereof. In another embodiment, a binding molecule of the invention comprises at least one heavy or light chain CDR of an antibody molecule. In another embodiment, a binding molecule of the invention comprises at least two CDRs from one or more antibody molecules. In another embodiment, a binding molecule of the invention comprises at least three CDRs from one or more antibody molecules. In another embodiment, a binding molecule of the invention comprises at least four CDRs from one or more antibody molecules. In another embodiment, a binding molecule of the invention comprises at least five CDRs from one or more antibody molecules. In another embodiment, a binding molecule of the invention comprises at least six CDRs from one or more antibody molecules.

The present invention is directed to a method of inhibiting angiogenesis in a subject, e.g., cancer patient, comprising administering to the subject an anti-SEMA4D and/or anti-VEGF binding molecule, e.g., an antibody, or antigen-binding fragment, variant, or derivative thereof. Unless specifically referring to full-sized antibodies such as naturally occurring antibodies, the terms "anti-SEMA4D antibody" and "anti-VEGF antibody" encompass full-sized antibodies as well as antigen-binding fragments, variants, analogs, or derivatives of such antibodies, e.g., naturally occurring antibody or immunoglobulin molecules or engineered antibody molecules or fragments that bind antigen in a manner similar to antibody molecules.

As used herein, "human" or "fully human" antibodies include antibodies having the amino acid sequence of a human immunoglobulin and include antibodies isolated from human immunoglobulin libraries or from animals transgenic for one or more human immunoglobulins and that do not express endogenous immunoglobulins, as described infra and, for example, in U.S. Pat. No. 5,939,598 by Kucherlapati et al. "Human" or "fully human" antibodies also include antibodies comprising at least the variable domain of a heavy chain, or at least the variable domains of a heavy chain and a light chain, where the variable domain(s) have the amino acid sequence of human immunoglobulin variable domain(s).

"Human" or "fully human" antibodies also include "human" or "fully human" antibodies, as described above, that comprise, consist essentially of, or consist of, variants (including derivatives) of antibody molecules (e.g., the VH regions and/or VL regions) described herein, which antibodies or fragments thereof immunospecifically bind to a SEMA4D or VEGF polypeptide or fragment or variant thereof. Standard techniques known to those of skill in the art can be used to introduce mutations in the nucleotide sequence encoding a human anti-SEMA4D antibody, including, but not limited to, site-directed mutagenesis and PCR-mediated mutagenesis which result in amino acid substitutions. Preferably, the variants (including derivatives) encode less than 50 amino acid substitutions, less than 40 amino acid substitutions, less than 30 amino acid substitutions, less than 25 amino acid substitutions, less than 20 amino acid substitutions, less than 15 amino acid substitutions, less than 10 amino acid substitutions, less than 5 amino acid substitutions, less than 4 amino acid substitutions, less than 3 amino acid substitutions, or less than 2 amino acid substitutions relative to the reference VH region, VHCDR1, VHCDR2, VHCDR3, VL region, VLCDR1, VLCDR2, or VLCDR3.

In certain embodiments, the amino acid substitutions are conservative amino acid substitution, discussed further below. Alternatively, mutations can be introduced randomly along all or part of the coding sequence, such as by saturation mutagenesis, and the resultant mutants can be screened for biological activity to identify mutants that retain activity (e.g., the ability to bind a SEMA4D or VEGF polypeptide, e.g., human, murine, or both human and murine SEMA4D or VEGF). Such variants (or derivatives thereof) of "human" or "fully human" antibodies can also be referred to as human or fully human antibodies that are "optimized" or "optimized for antigen binding" and include antibodies that have improved affinity to antigen.

The terms "antibody" and "immunoglobulin" are used interchangeably herein. An antibody or immunoglobulin comprises at least the variable domain of a heavy chain, and normally comprises at least the variable domains of a heavy chain and a light chain. Basic immunoglobulin structures in vertebrate systems are relatively well understood. See, e.g., Harlow et al. (1988) Antibodies: A Laboratory Manual (2nd ed.; Cold Spring Harbor Laboratory Press).

As used herein, the term "immunoglobulin" comprises various broad classes of polypeptides that can be distinguished biochemically. Those skilled in the art will appreciate that heavy chains are classified as gamma, mu, alpha, delta, or epsilon, ($\gamma$, $\mu$, $\alpha$, $\delta$, $\epsilon$) with some subclasses among them (e.g., $\gamma 1$-$\gamma 4$). It is the nature of this chain that determines the "class" of the antibody as IgG, IgM, IgA IgG, or IgE, respectively. The immunoglobulin subclasses (isotypes) e.g., IgG1, IgG2, IgG3, IgG4, IgA1, etc. are well characterized and are known to confer functional specialization. Modified versions of each of these classes and isotypes are readily discernable to the skilled artisan in view of the instant disclosure and, accordingly, are within the scope of the instant invention. All immunoglobulin classes are clearly within the scope of the present invention, the following discussion will generally be directed to the IgG class of immunoglobulin molecules. With regard to IgG, a standard immunoglobulin molecule comprises two identical light chain polypeptides of molecular weight approximately 23,000 Daltons, and two identical heavy chain polypeptides of molecular weight 53,000-70,000. The four chains are typically joined by disulfide bonds in a "Y" configuration wherein the light chains bracket the heavy chains starting at the mouth of the "Y" and continuing through the variable region.

Light chains are classified as either kappa or lambda ($\kappa$, $\lambda$). Each heavy chain class may be bound with either a kappa or lambda light chain. In general, the light and heavy chains are covalently bonded to each other, and the "tail" portions of the two heavy chains are bonded to each other by covalent disulfide linkages or non-covalent linkages when the immunoglobulins are generated either by hybridomas, B cells or genetically engineered host cells. In the heavy chain, the amino acid sequences run from an N-terminus at the forked ends of the Y configuration to the C-terminus at the bottom of each chain.

Both the light and heavy chains are divided into regions of structural and functional homology. The terms "constant" and "variable" are used functionally. In this regard, it will be appreciated that the variable domains of both the light (VL or VK) and heavy (VH) chain portions determine antigen recognition and specificity. Conversely, the constant domains of the light chain (CL) and the heavy chain (CH1, CH2 or CH3) confer important biological properties such as secretion, transplacental mobility, Fc receptor binding, complement binding, and the like. By convention the numbering of the constant region domains increases as they become more distal from the antigen binding site or amino-terminus of the antibody. The N-terminal portion is a variable region and at the C-terminal portion is a constant region; the CH3 and CL domains actually comprise the carboxy-terminus of the heavy and light chain, respectively.

As indicated above, the variable region allows the antibody to selectively recognize and specifically bind epitopes on antigens. That is, the VL domain and VH domain, or subset of the complementarity determining regions (CDRs) within these variable domains, of an antibody combine to form the variable region that defines a three dimensional antigen binding site. This quaternary antibody structure forms the antigen binding site present at the end of each arm of the Y. More specifically, the antigen binding site is defined by three CDRs on each of the VH and VL chains. In some instances, e.g., certain immunoglobulin molecules derived from camelid species or engineered based on camelid immunoglobulins, a complete immunoglobulin molecule may consist of heavy chains only, with no light chains. See, e.g., Hamers-Casterman et al., *Nature* 363:446-448 (1993).

In naturally occurring antibodies, the six "complementarity determining regions" or "CDRs" present in each antigen binding domain are short, non-contiguous sequences of amino acids that are specifically positioned to form the antigen binding domain as the antibody assumes its three dimensional configuration in an aqueous environment. The remainder of the amino acids in the antigen binding domains, referred to as "framework" regions, show less inter-molecular variability. The framework regions largely adopt a β-sheet conformation and the CDRs form loops that connect, and in some cases form part of, the β-sheet structure. Thus, framework regions act to form a scaffold that provides for positioning the CDRs in correct orientation by inter-chain, non-covalent interactions. The antigen binding domain formed by the positioned CDRs defines a surface complementary to the epitope on the immunoreactive antigen. This complementary surface promotes the non-covalent binding of the antibody to its cognate epitope. The amino acids comprising the CDRs and the framework regions, respectively, can be readily identified for any given heavy or light chain variable domain by one of ordinary skill in the art, since they have been precisely defined (see below).

In the case where there are two or more definitions of a term that is used and/or accepted within the art, the definition of the term as used herein is intended to include all such meanings unless explicitly stated to the contrary. A specific example is the use of the term "complementarity determining region" ("CDR") to describe the non-contiguous antigen combining sites found within the variable region of both heavy and light chain polypeptides. This particular region has been described by Kabat et al. (1983) U.S. Dept. of Health and Human Services, "Sequences of Proteins of Immunological Interest" and by Chothia and Lesk, *J. Mol. Biol.* 196:901-917 (1987), which are incorporated herein by reference, where the definitions include overlapping or subsets of amino acid residues when compared against each other. Nevertheless, application of either definition to refer to a CDR of an antibody or variants thereof is intended to be within the scope of the term as defined and used herein. The appropriate amino acid residues that encompass the CDRs as defined by each of the above cited references are set forth below in Table 1 as a comparison. The exact residue numbers that encompass a particular CDR will vary depending on the sequence and size of the CDR. Those skilled in the art can routinely determine which residues comprise a particular CDR given the variable region amino acid sequence of the antibody.

TABLE 1

CDR Definitions[1]

|  | Kabat | Chothia |
|---|---|---|
| VH CDR1 | 31-35 | 26-32 |
| VH CDR2 | 50-65 | 52-58 |
| VH CDR3 | 95-102 | 95-102 |
| VL CDR1 | 24-34 | 26-32 |
| VL CDR2 | 50-56 | 50-52 |
| VL CDR3 | 89-97 | 91-96 |

[1]Numbering of all CDR definitions in Table 1 is according to the numbering conventions set forth by Kabat et al. (see below).

Kabat et al. also defined a numbering system for variable domain sequences that is applicable to any antibody. One of ordinary skill in the art can unambiguously assign this system of "Kabat numbering" to any variable domain sequence, without reliance on any experimental data beyond the sequence itself. As used herein, "Kabat numbering" refers to the numbering system set forth by Kabat et al. (1983) U.S. Dept. of Health and Human Services, "Sequence of Proteins of Immunological Interest." Unless otherwise specified, references to the numbering of specific amino acid residue positions in an anti-SEMA4D or anti-VEGF antibody or antigen-binding fragment, variant, or derivative thereof of the present invention are according to the Kabat numbering system.

Antibodies or antigen-binding fragments, variants, or derivatives thereof of the invention include, but are not limited to, polyclonal, monoclonal, multispecific, bispecific, human, humanized, primatized, or chimeric antibodies, single-chain antibodies, epitope-binding fragments, e.g., Fab, Fab' and F(ab')$_2$, Fd, Fvs, single-chain Fvs (scFv), disulfide-linked Fvs (sdFv), fragments comprising either a VL or VH domain, fragments produced by a Fab expression library, and anti-idiotypic (anti-Id) antibodies (including, e.g., anti-Id antibodies to anti-SEMA4D antibodies disclosed herein). ScFv molecules are known in the art and are described, e.g., in U.S. Pat. No. 5,892,019. Immunoglobulin or antibody molecules of the invention can be of any type (e.g., IgG, IgE, IgM, IgD, IgA, and IgY), class (e.g., IgG1, IgG2, IgG3, IgG4, IgA1, and IgA2, etc.), or subclass of immunoglobulin molecule.

As used herein, the term "heavy chain portion" includes amino acid sequences derived from an immunoglobulin heavy chain. In certain embodiments, a polypeptide comprising a heavy chain portion comprises at least one of: a VH domain, a CH1 domain, a hinge (e.g., upper, middle, and/or lower hinge region) domain, a CH2 domain, a CH3 domain, or a variant or fragment thereof. For example, a binding polypeptide for use in the invention may comprise a polypeptide chain comprising a CH1 domain; a polypeptide chain comprising a CH1 domain, at least a portion of a hinge domain, and a CH2 domain; a polypeptide chain comprising a CH1 domain and a CH3 domain; a polypeptide chain comprising a CH1 domain, at least a portion of a hinge domain, and a CH3 domain, or a polypeptide chain comprising a CH1 domain, at least a portion of a hinge domain, a CH2 domain, and a CH3 domain. In another embodiment, a polypeptide of the invention comprises a polypeptide chain comprising a CH3 domain. Further, a binding polypeptide for use in the invention may lack at least a portion of a CH2 domain (e.g., all or part of a CH2 domain). As set forth above, it will be understood by one of ordinary skill in the art that these domains (e.g., the heavy chain portions) may be modified such that they vary in amino acid sequence from the naturally occurring immunoglobulin molecule.

In certain anti-SEMA4D or anti-VEGF antibodies, or antigen-binding fragments, variants, or derivatives thereof disclosed herein, the heavy chain portions of one polypeptide chain of a multimer are identical to those on a second polypeptide chain of the multimer. Alternatively, heavy chain portion-containing monomers of the invention are not identical. For example, each monomer may comprise a different target binding site, forming, for example, a bispecific antibody.

The heavy chain portions of a binding molecule for use in the methods disclosed herein may be derived from different immunoglobulin molecules. For example, a heavy chain portion of a polypeptide can comprise a $C_{H1}$ domain derived from an IgG1 molecule and a hinge region derived from an IgG3 molecule. In another example, a heavy chain portion can comprise a hinge region derived, in part, from an IgG1 molecule and, in part, from an IgG3 molecule. In another example, a heavy chain portion can comprise a chimeric hinge derived, in part, from an IgG1 molecule and, in part, from an IgG4 molecule.

As used herein, the term "light chain portion" includes amino acid sequences derived from an immunoglobulin light chain, e.g., a kappa or lambda light chain. Preferably, the light chain portion comprises at least one of a VL or CL domain.

Anti-SEMA4D or anti-VEGF antibodies, or antigen-binding fragments, variants, or derivatives thereof disclosed herein may be described or specified in terms of the epitope(s) or portion(s) of an antigen, e.g., a target polypeptide disclosed herein (e.g., SEMA4D or VEGF) that they recognize or specifically bind. The portion of a target polypeptide that specifically interacts with the antigen binding domain of an antibody is an "epitope," or an "antigenic determinant." A target polypeptide can comprise a single epitope, but typically comprises at least two epitopes, and can include any number of epitopes, depending on the size, conformation, and type of antigen. Furthermore, it should be noted that an "epitope" on a target polypeptide may be or may include non-polypeptide elements, e.g., an epitope may include a carbohydrate side chain.

The minimum size of a peptide or polypeptide epitope for an antibody is thought to be about four to five amino acids. Peptide or polypeptide epitopes preferably contain at least seven, more preferably at least nine and most preferably between at least about 15 to about 30 amino acids. Since a CDR can recognize an antigenic peptide or polypeptide in its tertiary form, the amino acids comprising an epitope need not be contiguous, and in some cases, may not even be on the same peptide chain. A peptide or polypeptide epitope recognized by anti-SEMA4D or anti-VEGF antibodies of the present invention may contain a sequence of at least 4, at least 5, at least 6, at least 7, more preferably at least 8, at least 9, at least 10, at least 15, at least 20, at least 25, or between about 15 to about 30 contiguous or non-contiguous amino acids of SEMA4D or VEGF, respectively.

By "specifically binds," it is generally meant that an antibody binds to an epitope via its antigen binding domain, and that the binding entails some complementarity between the antigen binding domain and the epitope. According to this definition, an antibody is said to "specifically bind" to an epitope when it binds to that epitope, via its antigen binding domain more readily than it would bind to a random, unrelated epitope. The term "specificity" is used herein to qualify the relative affinity by which a certain antibody binds to a certain epitope. For example, antibody "A" may be deemed to have a higher specificity for a given epitope than antibody "B," or antibody "A" may be said to bind to epitope "C" with a higher specificity than it has for related epitope "D."

By "preferentially binds," it is meant that the antibody specifically binds to an epitope more readily than it would bind to a related, similar, homologous, or analogous epitope. Thus, an antibody that "preferentially binds" to a given epitope would more likely bind to that epitope than to a related epitope, even though such an antibody may cross-react with the related epitope.

By way of non-limiting example, an antibody may be considered to bind a first epitope preferentially if it binds said first epitope with a dissociation constant ($K_D$) that is less than the antibody's $K_D$ for the second epitope. In another non-limiting example, an antibody may be considered to bind a first antigen preferentially if it binds the first epitope with an affinity that is at least one order of magnitude less than the antibody's $K_D$ for the second epitope. In another non-limiting example, an antibody may be considered to bind a first epitope preferentially if it binds the first epitope with an affinity that is at least two orders of magnitude less than the antibody's $K_D$ for the second epitope.

In another non-limiting example, an antibody may be considered to bind a first epitope preferentially if it binds the first epitope with an off rate (k(off)) that is less than the antibody's k(off) for the second epitope. In another non-limiting example, an antibody may be considered to bind a first epitope preferentially if it binds the first epitope with an affinity that is at least one order of magnitude less than the antibody's k(off) for the second epitope. In another non-limiting example, an antibody may be considered to bind a first epitope preferentially if it binds the first epitope with an affinity that is at least two orders of magnitude less than the antibody's k(off) for the second epitope.

An antibody is said to competitively inhibit binding of a reference antibody to a given epitope if it preferentially binds to that epitope to the extent that it blocks, to some degree, binding of the reference antibody to the epitope. Competitive inhibition may be determined by any method known in the art, for example, competition ELISA assays. An antibody may be said to competitively inhibit binding of the reference antibody to a given epitope by at least 90%, at least 80%, at least 70%, at least 60%, or at least 50%.

As used herein, the term "affinity" refers to a measure of the strength of the binding of an individual epitope with the CDR of an immunoglobulin molecule. See, e.g., Harlow et al. (1988) Antibodies: A Laboratory Manual (Cold Spring Harbor Laboratory Press, 2nd ed.) pages 27-28. As used herein, the term "avidity" refers to the overall stability of the complex between a population of immunoglobulins and an antigen, that is, the functional combining strength of an immunoglobulin mixture with the antigen. See, e.g., Harlow at pages 29-34. Avidity is related to both the affinity of individual immunoglobulin molecules in the population with specific epitopes, and also the valencies of the immunoglobulins and the antigen. For example, the interaction between a bivalent monoclonal antibody and an antigen with a highly repeating epitope structure, such as a polymer, would be one of high avidity.

Anti-SEMA4D and anti-VEGF antibodies or antigen-binding fragments, variants, or derivatives thereof of the invention may also be described or specified in terms of their cross-reactivity. As used herein, the term "cross-reactivity" refers to the ability of an antibody, specific for one antigen, to react with a second antigen; a measure of relatedness between two different antigenic substances. Thus, an antibody is cross reactive if it binds to an epitope other than the one that induced its formation. The cross reactive epitope generally contains many of the same complementary structural features as the inducing epitope, and in some cases, may actually fit better than the original.

For example, certain antibodies have some degree of cross-reactivity, in that they bind related, but non-identical epitopes, e.g., epitopes with at least 95%, at least 90%, at least 85%, at least 80%, at least 75%, at least 70%, at least 65%, at least 60%, at least 55%, and at least 50% identity (as calculated using methods known in the art and described herein) to a reference epitope. An antibody may be said to have little or no cross-reactivity if it does not bind epitopes with less than 95%, less than 90%, less than 85%, less than 80%, less than 75%, less than 70%, less than 65%, less than 60%, less than 55%, and less than 50% identity (as calculated using methods known in the art and described herein) to a reference epitope. An antibody may be deemed "highly specific" for a certain epitope, if it does not bind any other analog, ortholog, or homolog of that epitope.

Anti-SEMA4D and anti-VEGF binding molecules, e.g., antibodies or antigen-binding fragments, variants or derivatives thereof, of the invention may also be described or specified in terms of their binding affinity to a polypeptide of the invention, e.g., SEMA4D or VEGF, e.g., human, murine, or both human and murine SEMA4D or VEGF. Preferred binding affinities include those with a dissociation constant or Kd less than $5 \times 10^{-2}$ M, $10^{-2}$ M, $5 \times 10^{-3}$ M, $10^{-3}$ M, $5 \times 10^{-4}$ M, $10^{-4}$ M, $5 \times 10^{-5}$ M, $10^{-5}$ M, $5 \times 10^{-6}$ M, $10^{-6}$ M, $5 \times 10^{-7}$ M, $10^{-7}$ M, $5 \times 10^{-8}$ M, $10^{-8}$ M, $5 \times 10^{-9}$ M, $10^{-9}$ M, $5 \times 10^{-10}$ M, $10^{-10}$ M, $5 \times 10^{-11}$ M, $10^{-11}$ M, $5 \times 10^{-12}$ M, $10^{-12}$ M, $5 \times 10^{-13}$ M, $10^{-13}$ M, $5 \times 10^{-14}$ M, $10^{-14}$ M, $5 \times 10^{-15}$ M, or $10^{-15}$ M. In certain embodiments, the anti-SEMA4D or anti-VEGF binding molecule, e.g., an antibody or antigen binding fragment thereof, of the invention binds human SEMA4D or VEGF, respectively, with a Kd of about $5 \times 10^{-9}$ to about $6 \times 10^{-9}$. In another embodiment, the anti-SEMA4D or anti-VEGF binding molecule, e.g., an antibody or antigen binding fragment thereof, of the invention binds murine SEMA4D or VEGF, respectively, with a Kd of about $1 \times 10^{-9}$ to about $2 \times 10^{-9}$.

As used herein, the term "chimeric antibody" will be held to mean any antibody wherein the immunoreactive region or site is obtained or derived from a first species and the constant region (which may be intact, partial or modified in accordance with the instant invention) is obtained from a second species. In preferred embodiments the target binding region or site will be from a non-human source (e.g., mouse or primate) and the constant region is human.

As used herein, the term "engineered antibody" refers to an antibody in which the variable domain in either the heavy or light chain or both is altered by at least partial replacement of one or more CDRs from an antibody of known specificity and, if necessary, by partial framework region replacement and sequence changing. Although the CDRs may be derived from an antibody of the same class or even subclass as the antibody from which the framework regions are derived, it is envisaged that the CDRs will be derived from an antibody of different class and preferably from an antibody from a different species. An engineered antibody in which one or more "donor" CDRs from a non-human antibody of known specificity is grafted into a human heavy or light chain framework region is referred to herein as a "humanized antibody." It may not be necessary to replace all of the CDRs with the complete CDRs from the donor variable domain to transfer the antigen binding capacity of one variable domain to another. Rather, it may only be necessary to transfer those residues that are necessary to maintain the activity of the target binding site.

It is further recognized that the framework regions within the variable domain in a heavy or light chain, or both, of a humanized antibody may comprise solely residues of human origin, in which case these framework regions of the humanized antibody are referred to as "fully human framework regions" (for example, MAb VX15/2503, disclosed in U.S. Patent Appl. Publication No. US 2010/0285036 A1 as MAb 2503, incorporated herein by reference in its entirety). Alternatively, one or more residues of the framework region(s) of the donor variable domain can be engineered within the corresponding position of the human framework region(s) of a variable domain in a heavy or light chain, or both, of a humanized antibody if necessary to maintain proper binding or to enhance binding to the SEMA4D antigen. A human framework region that has been engineered in this manner would thus comprise a mixture of human and donor framework residues, and is referred to herein as a "partially human framework region."

For example, humanization of an anti-SEMA4D antibody can be essentially performed following the method of Winter and co-workers (Jones et al., Nature 321:522-525 (1986); Riechmann et al., Nature 332:323-327 (1988); Verhoeyen et al., Science 239:1534-1536 (1988)), by substituting rodent or mutant rodent CDRs or CDR sequences for the corresponding sequences of a human anti-SEMA4D antibody. See also U.S. Pat. Nos. 5,225,539; 5,585,089; 5,693,761; 5,693,762; 5,859,205; herein incorporated by reference. The resulting humanized anti-SEMA4D antibody would comprise at least one rodent or mutant rodent CDR within the fully human framework regions of the variable domain of the heavy and/or light chain of the humanized antibody. In some instances, residues within the framework regions of one or more variable domains of the humanized anti-SEMA4D antibody are replaced by corresponding non-human (for example, rodent) residues (see, for example, U.S. Pat. Nos. 5,585,089; 5,693,761; 5,693,762; and 6,180,370), in which case the resulting humanized anti-SEMA4D antibody would comprise partially human framework regions within the variable domain of the heavy and/or light chain. Similar methods can be used for humanization of an anti-VEGF antibody.

Furthermore, humanized antibodies can comprise residues that are not found in the recipient antibody or in the donor antibody. These modifications are made to further refine antibody performance (e.g., to obtain desired affinity). In general, the humanized antibody will comprise substantially all of at least one, and typically two, variable domains, in which all or substantially all of the CDRs correspond to those of a non-human immunoglobulin and all or substantially all of the framework regions are those of a human immunoglobulin sequence. The humanized antibody optionally also will comprise at least a portion of an immunoglobulin constant region (Fc), typically that of a human immunoglobulin. For further details see Jones et al., Nature 331:522-525 (1986); Riechmann et al., Nature 332:323-329 (1988); and Presta, Curr. Op. Struct. Biol. 2:593-596 (1992); herein incorporated by reference. Accordingly, such "humanized" antibodies may include antibodies wherein substantially less than an intact human variable domain has been substituted by the corresponding sequence from a non-human species. In practice, humanized antibodies are typically human antibodies in which some CDR residues and possibly some framework residues are substituted by residues from analogous sites in rodent antibodies. See, for example, U.S. Pat. Nos. 5,225,539; 5,585,089; 5,693,761; 5,693,762; 5,859,205. See also U.S. Pat. No. 6,180,370, and International Publication No. WO 01/27160, where humanized antibodies and techniques for producing humanized antibodies having improved affinity for a predetermined antigen are disclosed.

II. Target Polypeptide Description—SEMA4D

As used herein, the terms "semaphorin-4D", "SEMA4D", and "SEMA4D polypeptide" are used interchangeably, as are "SEMA4D" and "Sema4D." In certain embodiments, SEMA4D is expressed on the surface of or secreted by a cell. In another embodiment, SEMA4D is membrane bound. In another embodiment, SEMA4D is soluble, e.g., sSEMA4D. In another embodiment, SEMA4D may include a full-sized SEMA4D or a fragment thereof, or a SEMA4D variant polypeptide, wherein the fragment of SEMA4D or SEMA4D variant polypeptide retains some or all functional properties of the full-sized SEMA4D.

The full-sized human SEMA4D protein is a homodimeric transmembrane protein consisting of two polypeptide chains of 150 kDa. SEMA4D belongs to the semaphorin family of cell surface receptors and is also referred to as CD100. Both human and mouse SEMA4D/Sema4D are proteolytically cleaved from their transmembrane form to generate 120-kDa soluble forms, indicating the existence of two Sema4D isoforms (Kumanogoh et al., *J. Cell Science* 116(7):3464 (2003)). Semaphorins consist of soluble and membrane-bound proteins that were originally defined as axonal-guidance factors which play an important role in establishing precise connections between neurons and their appropriate target. Structurally considered a class IV semaphorin, SEMA4D consists of an amino-terminal signal sequence followed by a characteristic 'Sema' domain, which contains 17 conserved cysteine residues, an Ig-like domain, a lysine-rich stretch, a hydrophobic transmembrane region, and a cytoplasmic tail.

Each polypeptide chain of SEMA4D includes a signal sequence of about 13 amino acids followed by a semaphorin domain of about 512 amino acids, an immunoglobulin-like (Ig-like) domain of about 65 amino acids, a lysine-rich stretch of 104 amino acids, a hydrophobic transmembrane region of about 19 amino acids, and a cytoplasmic tail of 110 amino acids. A consensus site for tyrosine phosphorylation in the cytoplasmic tail supports the predicted association of SEMA4D with a tyrosine kinase (Schlossman et al., Eds. (1995) Leucocyte Typing V (Oxford University Press, Oxford).

SEMA4D is known to have at least two functional receptors. One of the receptors, Plexin-B1, is expressed in non-lymphoid tissues and has been shown to be a high affinity (1 nM) receptor for SEMA4D (Tamagnone et al., *Cell* 99:71-80 (1999)). SEMA4D stimulation of Plexin B1 signaling has been shown to induce growth cone collapse of neurons, and to induce process extension collapse and apoptosis of oligodendrocytes (Giraudon et al., *J. Immunol.* 172:1246-1255 (2004); Giraudon et al., *NeuroMolecular Med.* 7:207-216 (2005)). After binding to SEMA4D, Plexin B1 signaling mediates the inactivation of R-Ras, leading to a decrease in the integrin mediated attachment to the extracellular matrix, as well as to activation of RhoA, leading to cell collapse by reorganization of the cytoskeleton. See Kruger et al., *Nature Rev. Mol. Cell Biol.* 6:789-800 (2005); Pasterkamp, *TRENDS in Cell Biology* 15:61-64 (2005)).

In lymphoid tissues, CD72 is utilized as a low affinity (300 nM) SEMA4D receptor (Kumanogoh et al., *Immunity* 13:621-631 (2000)). B cells and Antigen Presenting Cells (APC) express CD72, and anti-CD72 antibodies have many of the same effects as sSEMA4D, such as enhancement of CD40-induced B cell responses and B cell shedding of CD23. CD72 is thought to act as a negative regulator of B cell responses by recruiting the tyrosine phosphatase SHP-1, which can associate with many inhibitory receptors. Interaction of SEMA4D with CD72 results in the dissociation of SHP-1, and the loss of this negative activation signal. SEMA4D has been shown to promote T cell stimulation and B cell aggregation and survival in vitro. The addition of SEMA4D-expressing cells or sSEMA4D enhances CD40-induced B cell proliferation and immunoglobulin production in vitro, and accelerates in vivo antibody responses (Ishida et al., *Inter. Immunol.* 15:1027-1034 (2003); Kumanogoh and H. Kukutani, *Trends in Immunol.* 22:670-676 (2001)). sSEMA4D enhances the CD40 induced maturation of DCs, including up-regulation of costimulatory molecules and increased secretion of IL-12. In addition, sSEMA4D can inhibit immune cell migration, which can be reversed by addition of blocking anti-SEMA4D mouse antibodies (Elhabazi et al., *J. Immunol.* 166:4341-4347 (2001); Delaire et al., *J. Immunol.* 166:4348-4354 (2001)).

Sema4D is expressed at high levels in lymphoid organs, including the spleen, thymus, and lymph nodes, and in non-lymphoid organs, such as the brain, heart, and kidney. In lymphoid organs, Sema4D is abundantly expressed on resting T cells but only weakly expressed on resting B cells and antigen-presenting cells (APCs), such as dendritic cells (DCs).

Cellular activation increases the surface expression of SEMA4D as well as the generation of soluble SEMA4D (sSEMA4D). The expression pattern of SEMA4D suggests that it plays an important physiological as well as pathological role in the immune system. SEMA4D has been shown to promote B cell activation, aggregation and survival; enhance CD40-induced proliferation and antibody production; enhance antibody response to T cell dependent antigens; increase T cell proliferation; enhance dendritic cell maturation and ability to stimulate T cells; and is directly implicated in demyelination and axonal degeneration (Shi et al., *Immunity* 13:633-642 (2000); Kumanogoh et al., *J Immunol* 169: 1175-1181 (2002); and Watanabe et al., *J Immunol* 167:4321-4328 (2001)).

SEMA4D knock out (SEMA4D−/−) mice have provided additional evidence that SEMA4D plays an important role in both humoral and cellular immune responses. There are no known abnormalities of non-lymphoid tissues in SEMA4D−/− mice. Dendritic cells (DCs) from the SEMA4D−/− mice have poor allostimulatory ability and show defects in expression of costimulatory molecules, which can be rescued by the addition of sSEMA4D. Mice deficient in SEMA4D (SEMA4D−/−) fail to develop experimental autoimmune encephalomyelitis induced by myelin oligodendrocyte glycoprotein peptide, because myelin oligodendrocyte glycoprotein-specific T cells are poorly generated in the absence of SEMA4D (Kumanogoh et al., *J Immunol* 169:1175-1181 (2002)). A significant amount of soluble SEMA4D is also detected in the sera of autoimmunity-prone MRL/lpr mice (model of systemic autoimmune diseases such as SLE), but not in normal mice. Further, the levels of sSEMA4D correlate with levels of auto-antibodies and increase with age (Wang et al., *Blood* 97:3498-3504 (2001)). Soluble SEMA4D has also been shown to accumulate in the cerebral spinal fluid and sera of patients with demyelinating disease, and sSEMA4D induces apoptosis of human pluripotent neural precursors (Dev cells), and both inhibits process extension and induces apoptosis of rat oligodendrocytes in vitro (Giraudon et al., *J Immunol* 172(2):1246-1255 (2004)). This apoptosis was blocked by an anti-SEMA4D monoclonal antibody (MAb).

III. Anti-SEMA4D Antibodies

Antibodies that bind SEMA4D have been described in the art. See, for example, US Publ. Nos. 2008/0219971 A1, US 2010/0285036 A1, and US 2006/0233793 A1, International Patent Applications WO 93/14125, WO 2008/100995, and WO 2010/129917, and Herold et al., *Int. Immunol.* 7(1): 1-8 (1995), each of which is herein incorporated in its entirety by reference.

The invention generally relates to a method of inhibiting angiogenesis in a subject, e.g., a human cancer patient or a patient with wet age-related macular degeneration (AMD), comprising administration of an antibody which specifically binds to SEMA4D, or an antigen-binding fragment, variant, or derivative thereof. In certain embodiments, the antibody blocks the interaction of SEMA4D with one or more of its receptors, e.g., Plexin-B1. In certain embodiments the cancer cells express Plexin-B1. Anti-SEMA4D antibodies having these properties can be used in the methods provided herein. Antibodies that can be used include, but are not limited to MAbs VX15/2503, 67, and 76 and antigen-binding fragments, variants, or derivatives thereof which are fully described in US 2010/0285036 A1. Additional antibodies which can be used in the methods provided herein include the BD16 antibody described in US 2006/0233793 A1 as well as antigen-binding fragments, variants, or derivatives thereof; or any of MAb 301, MAb 1893, MAb 657, MAb 1807, MAb 1656, MAb 1808, Mab 59, MAb 2191, MAb 2274, MAb 2275, MAb 2276, MAb 2277, MAb 2278, MAb 2279, MAb 2280, MAb 2281, MAb 2282, MAb 2283, MAb 2284, and MAb 2285, as well as any fragments, variants or derivatives thereof as described in US 2008/0219971 A1. In certain embodiments an anti-SEMA4D antibody for use in the methods provided herein binds human, murine, or both human and murine SEMA4D. Also useful are antibodies which bind to the same epitope as any of the aforementioned antibodies and/or antibodies which competitively inhibit binding or activity of any of the aforementioned antibodies.

In certain embodiments, an anti-SEMA4D antibody or antigen-binding fragment, variant, or derivative thereof useful in the methods provided herein has an amino acid sequence that has at least about 80%, about 85%, about 88%, about 89%, about 90%, about 91%, about 92%, about 93%, about 94%, or about 95% sequence identity to the amino acid sequence for a reference anti-SEMA4D antibody molecule, for example, those described above. In a further embodiment, the binding molecule shares at least about 96%, about 97%, about 98%, about 99%, or 100% sequence identity to a reference antibody.

In another embodiment, an anti-SEMA4D antibody or antigen-binding fragment, variant, or derivative thereof useful in the methods provided herein comprises, consists essentially of, or consists of an immunoglobulin heavy chain variable domain (VH domain), where at least one of the CDRs of the VH domain has an amino acid sequence that is at least about 80%, about 85%, about 90%, about 95%, about 96%, about 97%, about 98%, about 99%, or identical to CDR1, CDR2 or CDR3 of SEQ ID NO: 9 or 10.

In another embodiment, an anti-SEMA4D antibody or antigen-binding fragment, variant, or derivative thereof useful in the methods provided herein comprises, consists essentially of, or consists of an immunoglobulin heavy chain variable domain (VH domain), where at least one of the CDRs of the VH domain has an amino acid sequence that is at least about 80%, about 85%, about 90%, about 95%, about 96%, about 97%, about 98%, about 99%, or identical to SEQ ID NO: 6, SEQ ID NO: 7, or SEQ ID NO: 8.

In another embodiment, an anti-SEMA4D antibody or antigen-binding fragment, variant, or derivative thereof useful in the methods provided herein comprises, consists essentially of, or consists of an immunoglobulin heavy chain variable domain (VH domain), where at least one of the CDRs of the VH domain has an amino acid sequence identical, except for 1, 2, 3, 4, or 5 conservative amino acid substitutions, to SEQ ID NO: 6, SEQ ID NO: 7, or SEQ ID NO: 8.

In another embodiment, an anti-SEMA4D antibody or antigen-binding fragment, variant, or derivative thereof useful in the methods provided herein comprises, consists essentially of, or consists of a VH domain that has an amino acid sequence that is at least about 80%, about 85%, about 90%, about 91%, about 92%, about 93%, about 94%, about 95%, about 96%, about 97%, about 98%, about 99%, or 100% identical to SEQ ID NO: 9 or SEQ ID NO: 10, wherein an anti-SEMA4D antibody comprising the encoded VH domain specifically or preferentially binds to SEMA4D.

In another embodiment, an anti-SEMA4D antibody or antigen-binding fragment, variant, or derivative thereof useful in the methods provided herein comprises, consists essentially of, or consists of an immunoglobulin light chain variable domain (VL domain), where at least one of the CDRs of the VL domain has an amino acid sequence that is at least about 80%, about 85%, about 90%, about 95%, about 96%, about 97%, about 98%, about 99%, or identical to CDR1, CDR2 or CDR3 of SEQ ID NO: 17 or 18.

In another embodiment, an anti-SEMA4D antibody or antigen-binding fragment, variant, or derivative thereof useful in the methods provided herein comprises, consists essentially of, or consists of an immunoglobulin light chain variable domain (VL domain), where at least one of the CDRs of the VL domain has an amino acid sequence that is at least about 80%, about 85%, about 90%, about 95%, about 96%, about 97%, about 98%, about 99%, or identical to SEQ ID NO: 14, SEQ ID NO: 15, or SEQ ID NO: 16.

In another embodiment, an anti-SEMA4D antibody or antigen-binding fragment, variant, or derivative thereof useful in the methods provided herein comprises, consists essentially of, or consists of an immunoglobulin light chain variable domain (VL domain), where at least one of the CDRs of the VL domain has an amino acid sequence identical, except for 1, 2, 3, 4, or 5 conservative amino acid substitutions, to SEQ ID NO: 14, SEQ ID NO: 15, or SEQ ID NO: 16.

In a further embodiment, an anti-SEMA4D antibody or antigen-binding fragment, variant, or derivative thereof useful in the methods provided herein comprises, consists essentially of, or consists of a VL domain that has an amino acid sequence that is at least about 80%, about 85%, about 90%, about 91%, about 92%, about 93%, about 94%, about 95%, about 96%, about 97%, about 98%, about 99%, or 100% identical to SEQ ID NO: 17 or SEQ ID NO: 18, wherein an anti-SEMA4D antibody comprising the encoded VL domain specifically or preferentially binds to SEMA4D.

Also included for use in the methods provided herein are polypeptides encoding anti-SEMA4D antibodies, or antigen-binding fragments, variants, or derivatives thereof as described herein, polynucleotides encoding such polypeptides, vectors comprising such polynucleotides, and host cells comprising such vectors or polynucleotides, all for producing anti-SEMA4D antibodies, or antigen-binding fragments, variants, or derivatives thereof for use in the methods described herein.

Suitable biologically active variants of the anti-SEMA4D antibodies of the invention can be used in the methods of the present invention. Such variants will retain the desired binding properties of the parent anti-SEMA4D antibody. Methods for making antibody variants are generally available in the art.

Methods for mutagenesis and nucleotide sequence alterations are well known in the art. See, for example, Walker and Gaastra, eds. (1983) Techniques in Molecular Biology (MacMillan Publishing Company, New York); Kunkel, Proc. *Natl. Acad. Sci. USA* 82:488-492 (1985); Kunkel et al., *Methods Enzymol.* 154:367-382 (1987); Sambrook et al. (1989) Molecular Cloning: A Laboratory Manual (Cold Spring Harbor, N.Y.); U.S. Pat. No. 4,873,192; and the references cited therein; herein incorporated by reference. Guidance as to appropriate amino acid substitutions that do not affect biological activity of the polypeptide of interest may be found in the model of Dayhoff et al. (1978) in Atlas of Protein Sequence and Structure (Natl. Biomed. Res. Found., Washington, D.C.), pp. 345-352, herein incorporated by reference in its entirety. The model of Dayhoff et al. uses the Point Accepted Mutation (PAM) amino acid similarity matrix (PAM 250 matrix) to determine suitable conservative amino acid substitutions. Conservative substitutions, such as exchanging one amino acid with another having similar properties, may be preferred. Examples of conservative amino acid substitutions as taught by the PAM 250 matrix of the Dayhoff et al. model include, but are not limited to, Gly↔Ala, Val↔Ile↔Leu, Asp↔Glu, Lys↔Arg, Asn↔Gln, and Phe↔Trp↔Tyr.

In constructing variants of the anti-SEMA4D binding molecule, e.g., an antibody or antigen-binding fragment thereof, polypeptides of interest, modifications are made such that variants continue to possess the desired properties, e.g., being capable of specifically binding to a SEMA4D, e.g., human, murine, or both human and murine SEMA4D, e.g., expressed on the surface of or secreted by a cell and having SEMA4D blocking activity, as described herein. Obviously, any mutations made in the DNA encoding the variant polypeptide must not place the sequence out of reading frame and preferably will not create complementary regions that could produce secondary mRNA structure. See EP Patent Application Publication No. 75,444.

Methods for measuring anti-SEMA4D binding molecule, e.g., an antibody or antigen-binding fragment, variant, or derivative thereof, binding specificity include, but are not limited to, standard competitive binding assays, assays for monitoring immunoglobulin secretion by T cells or B cells, T cell proliferation assays, apoptosis assays, ELISA assays, and the like. See, for example, such assays disclosed in WO 93/14125; Shi et al., *Immunity* 13:633-642 (2000); Kumanogoh et al., *J Immunol* 169:1175-1181 (2002); Watanabe et al., *J Immunol* 167:4321-4328 (2001); Wang et al., *Blood* 97:3498-3504 (2001); and Giraudon et al., *J Immunol* 172(2): 1246-1255 (2004), all of which are herein incorporated by reference.

Methods for measuring the anti-angiogenic ability of an anti-SEMA4D antibody or antigen-binding fragment, variant, or derivative thereof are describe herein and are also well known in the art.

When discussed herein whether any particular polypeptide, including the constant regions, CDRs, VH domains, or VL domains disclosed herein, is at least about 65%, about 70%, about 75%, about 80%, about 85%, about 90%, about 91%, about 92%, about 93%, about 94%, about 95%, about 96%, about 97%, about 98%, about 99%, or even about 100% identical to another polypeptide, the % identity can be determined using methods and computer programs/software known in the art such as, but not limited to, the BESTFIT program (Wisconsin Sequence Analysis Package, Version 8 for Unix, Genetics Computer Group, University Research Park, 575 Science Drive, Madison, Wis. 53711). BESTFIT uses the local homology algorithm of Smith and Waterman (1981) Adv. Appl. Math. 2:482-489, to find the best segment of homology between two sequences. When using BESTFIT or any other sequence alignment program to determine whether a particular sequence is, for example, 95% identical to a reference sequence according to the present invention, the parameters are set, of course, such that the percentage of identity is calculated over the full length of the reference polypeptide sequence and that gaps in homology of up to 5% of the total number of amino acids in the reference sequence are allowed.

For purposes of the present invention, percent sequence identity may be determined using the Smith-Waterman homology search algorithm using an affine gap search with a gap open penalty of 12 and a gap extension penalty of 2, BLOSUM matrix of 62. The Smith-Waterman homology search algorithm is taught in Smith and Waterman (1981) Adv. Appl. Math. 2:482-489. A variant may, for example, differ from a reference anti-SEMA4D antibody (e.g., MAb VX15/2503, 67 or 76) by as few as 1 to 15 amino acid residues, as few as 1 to 10 amino acid residues, such as 6-10, as few as 5, as few as 4, 3, 2, or even 1 amino acid residue.

The constant region of an anti-SEMA4D antibody can be mutated to alter effector function in a number of ways. For example, see U.S. Pat. No. 6,737,056B1 and U.S. Patent Application Publication No. 2004/0132101A1, which disclose Fc mutations that optimize antibody binding to Fc receptors.

In certain anti-SEMA4D antibodies or fragments, variants or derivatives thereof useful in the methods provided herein, the Fc portion can be mutated to decrease effector function using techniques known in the art. For example, the deletion or inactivation (through point mutations or other means) of a constant region domain can reduce Fc receptor binding of the circulating modified antibody thereby increasing tumor localization. In other cases, constant region modifications consistent with the instant invention moderate complement binding and thus reduce the serum half-life. Yet other modifications of the constant region can be used to modify disulfide linkages or oligosaccharide moieties that allow for enhanced localization due to increased antigen specificity or antibody flexibility. The resulting physiological profile, bioavailability and other biochemical effects of the modifications, such as tumor localization, biodistribution and serum half-life, can easily be measured and quantified using well known immunological techniques without undue experimentation.

Anti-SEMA4D antibodies for use in the methods provided herein include derivatives that are modified, e.g., by the covalent attachment of any type of molecule to the antibody such that covalent attachment does not prevent the antibody from specifically binding to its cognate epitope. For example, but not by way of limitation, the antibody derivatives include antibodies that have been modified, e.g., by glycosylation, acetylation, pegylation, phosphorylation, amidation, derivatization by known protecting/blocking groups, proteolytic cleavage, linkage to a cellular ligand or other protein, etc. Any of numerous chemical modifications can be carried out by known techniques, including, but not limited to specific chemical cleavage, acetylation, formylation, etc. Additionally, the derivative can contain one or more non-classical amino acids.

A "conservative amino acid substitution" is one in which the amino acid residue is replaced with an amino acid residue having a side chain with a similar charge. Families of amino acid residues having side chains with similar charges have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Alternatively, mutations can be introduced randomly along all or part of the coding sequence, such as by saturation mutagenesis, and the resultant mutants can be screened for biological activity to identify mutants that retain activity (e.g., the ability to bind an anti-SEMA4D polypeptide, to block SEMA4D interaction with its receptor, or to inhibit angiogenesis in a subject, e.g., a cancer patient).

For example, it is possible to introduce mutations only in framework regions or only in CDR regions of an antibody molecule. Introduced mutations can be silent or neutral missense mutations, i.e., have no, or little, effect on an antibody's ability to bind antigen. These types of mutations can be useful to optimize codon usage, or improve a hybridoma's antibody production. Alternatively, non-neutral missense mutations may alter an antibody's ability to bind antigen. One of skill in the art would be able to design and test mutant molecules with desired properties such as no alteration in antigen binding activity or alteration in binding activity (e.g., improvements in antigen binding activity or change in antibody specificity). Following mutagenesis, the encoded protein may routinely be expressed and the functional and/or biological activity of the encoded protein, (e.g., ability to immunospecifically bind at least one epitope of a SEMA4D polypeptide) can be determined using techniques described herein or by routinely modifying techniques known in the art.

In certain embodiments, the anti-SEMA4D antibodies for use in the methods provided herein comprise at least one optimized complementarity-determining region (CDR). By "optimized CDR" is intended that the CDR has been modified and optimized to improve binding affinity and/or anti-SEMA4D activity that is imparted to an anti-SEMA4D antibody comprising the optimized CDR. "Anti-SEMA4D activity" or "SEMA4D blocking activity" can include activity which modulates one or more of the following activities associated with SEMA4D: B cell activation, aggregation and survival; CD40-induced proliferation and antibody production; antibody response to T cell dependent antigens; T cell or other immune cell proliferation; dendritic cell maturation; demyelination and axonal degeneration; apoptosis of pluripotent neural precursors and/or oligodendrocytes; induction of endothelial cell migration; inhibition of spontaneous monocyte migration; inhibition of tumor cell metastasis, binding to cell surface plexin B1 or other receptor, or any other activity association with soluble SEMA4D or SEMA4D that is expressed on the surface of SEMA4D+ cells. In a particular embodiment, anti-SEMA4D activity includes the ability to inhibit tumor angiogenesis, either in combination with inhibition of primary tumor cell growth and tumor metastases, or independently of primary tumor cell growth and tumor metastases. Anti-SEMA4D activity can also be attributed to a decrease in incidence or severity of diseases associated with SEMA4D expression, including, but not limited to, certain types of cancers including lymphomas, autoimmune diseases, inflammatory diseases including central nervous system (CNS) and peripheral nervous system (PNS) inflammatory diseases, transplant rejections, and invasive angiogenesis. Examples of optimized antibodies based on murine anti-SEMA4D MAb BD16 were described in US Publ. No. 2008/0219971 A1, International Patent Application WO 93/14125 and Herold et al., *Int. Immunol.* 7(1): 1-8 (1995), each of which are herein incorporated by reference in their entirety. The modifications may involve replacement of amino acid residues within the CDR such that an anti-SEMA4D antibody retains specificity for the SEMA4D antigen and has improved binding affinity and/or improved anti-SEMA4D activity.

IV. Target Polypeptide Description—VEGF

As used herein, the terms "VEGF" and "VEGF polypeptide" are used interchangeably. In certain embodiments, VEGF is secreted by a cell. In another embodiment, VEGF is membrane-bound or bound to the extracellular matrix. In another embodiment, VEGF is soluble. In other embodiments, VEGF may include a full-sized VEGF polylpeptide or a fragment thereof, or a VEGF variant polypeptide (including VEGF isoforms and splice variants), wherein the fragment of VEGF or VEGF variant polypeptide retains some or all functional properties of the full-sized, native VEGF.

The full-sized, native human VEGF protein is a homodimeric glycoprotein consisting of two identical 23 kDa polypeptide subunits. See, Ho and Kuo, *Int. J. Biochem Cell Biol.* 2007; 39(7-8): 1349-1357. The VEGF gene family has several members, including VEGF-A (also referred to herein as "VEGF"), VEGF-B, VEGF-C, VEGF-D, and P1GF. See, Ho and Kuo, *Int. J. Biochem Cell Biol.* 2007; 39(7-8): 1349-1357. There are numerous alternatively spliced isoforms of human VEGF, including $VEGF_{165}$, $VEGF_{121}$, $VEGF_{189}$, and $VEGF_{206}$, which have different bioavailabilities, bioactivities, and receptor specificities. See, Ho and Kuo, *Int. J. Biochem Cell Biol.* 2007; 39(7-8): 1349-1357; Ferrara et al., *Nature Med.* 2003; 9 (6):669-676. The $VEGF_{165}$ isoform is the most prevalent and mitogenic and is most similar in properties to the 45 kDa native VEGF. See, Ho and Kuo, *Int. J. Biochem Cell Biol.* 2007; 39(7-8): 1349-1357; Ferrara et al., *Nature Med.* 2003; 9 (6):669-676.

VEGF expression and activity is modulated by a number of factors, including hypoxia, mechanical forces, dysregulation of tumor suppressors and oncogenes, inflammatory mediators (e.g., cytokines), and other growth factors. See, Ho and Kuo, *Int. J. Biochem Cell Biol.* 2007; 39(7-8): 1349-1357. Once expressed, some secreted VEGF is sequestered by the extracellular matrix, which can act as a reservoir that releases VEGF through proteolysis. See, Ho and Kuo, *Int. J. Biochem Cell Biol.* 2007; 39(7-8): 1349-1357.

VEGF binds two receptor tyrosine kinases with high affinity—VEGFR1 (Flt-1) and VEGFR2 (KDR, Flk1)—which are found mainly on the surface of vascular endothelial cells. Gerber and Ferrara, *Cancer Res.* 2005; 65: 671-680. It is thought that only VEGFR-2 activation induces angiogenesis, mitogenesis, and increased vascular permeability through a process of autophosphorylation that activates downstream signaling pathways such as phosphatidylinositol 3'-OH kinase/Akt. Gerber and Ferrara, *Cancer Res.* 2005; 65: 671-680. VEGFR1 is thought to act as a decoy receptor that suppresses the availability of VEGF to VEGFR2, and may be important in hematopoiesis, matrix metalloproteinase development, and release of growth factors from endothelial cells. Gerber and Ferrara, *Cancer Res.* 2005; 65: 671-680.

Antagonism of VEGF with monoclonal antibodies has been shown to inhibit primary tumor growth, primarily by disrupting the blood supply to tumors and to inhibit tumor angiogenesis. Gerber and Ferrara, *Cancer Res.* 2005; 65: 671-680.

For reviews related to VEGF and VEGF inhibition, see Ferrara, *Nature Reviews* 2002; 2: 795-803; Ho and Kuo, *Int. J. Biochem Cell Biol.* 2007; 39(7-8): 1349-1357; Ferrara, et al., *Nature Med.* 2003; 9:669-676; Pander et al., *Drug Discovery Today* 2007; 12: 1054-1060; Hicklin and Ellis, *J. Clin. Oncol.* 2005; 5:1011-1027; and Gerber and Ferrara, *Cancer Res.* 2005; 65: 671-680 (each of which is incorporated herein by reference in its entirety).

V. Anti-VEGF Antibodies

Antibodies that bind VEGF have been described the art. See, for example, U.S. Pat. No. 6,884,879 and Presta et al., *Cancer Res.* 57: 4593-4599 (1997), each of which is herein incorporated in its entirety by reference.

The invention generally relates to a method of inhibiting angiogenesis in a subject, e.g., a human cancer patient, comprising administration of an antibody which specifically binds to VEGF or its VEGFR2 receptor, or an antigen-binding fragment, variant, or derivative thereof. In certain embodiments, the antibody blocks the interaction of VEGF with one or more of its receptors, e.g., VEGFR1 and VEGFR2. Anti-VEGF antibodies having these properties can be used in the methods provided herein.

The antibodies according to the invention comprise anti-VEGF or anti-VEGFR2 antibodies or antigen-binding fragments, variants, or derivatives thereof that bind to VEGF or its VEGFR2 receptor, e.g., MAb 7392 as described herein, and in International Patent Appl. No. PCT/US2011/040361, which is incorporated herein by reference in its entirety. In certain embodiments, the anti-VEGF antibodies bind human VEGF. In other embodiments, the anti-VEGF antibodies block VEGF binding to its receptor, e.g., VEGFR1 or VEGFR2. In certain embodiments, the anti-VEGF or anti-VEGFR2 antibodies block phosphorylation of VEGFR2 by VEGF.

In one embodiment, the present invention provides an isolated binding molecule, e.g., an antibody or antigen binding fragment thereof, which specifically binds to the same VEGF epitope as MAb7392. In another embodiment, the present invention provides an isolated binding molecule, e.g., an antibody or antigen binding fragment thereof that specifically binds to VEGF, and competitively inhibits MAb 7392 from specifically binding to VEGF. In certain embodiments, the antibody specifically binds VEGF with an affinity of less than about 3.9×10−9 M. In another embodiment, the antibody specifically binds VEGF with an affinity of less than about 9.1×10−10 M.

In one embodiment, the present invention provides an isolated antibody or antigen-binding fragment thereof comprising, consisting essentially of, or consisting of an immunoglobulin heavy chain variable domain (VH domain), where at least one of the CDRs of the VH domain has an amino acid sequence that is identical to CDR1, CDR2 or CDR3 of SEQ ID NO:41.

In another embodiment, the present invention provides an isolated antibody or antigen-binding fragment thereof comprising, consisting essentially of, or consisting of an immunoglobulin heavy chain variable domain (VH domain), where at least one of the CDRs of the VH domain has an amino acid sequence that is identical to SEQ ID NO: 43, SEQ ID NO: 44, or SEQ ID NO: 45.

In another embodiment, the present invention provides an isolated antibody or antigen-binding fragment thereof comprising, consisting essentially of, or consisting of a VH domain that has an amino acid sequence that is identical to SEQ ID NO:41, wherein an anti-VEGF antibody comprising the encoded VH domain specifically or preferentially binds to VEGF, more specifically, human VEGF.

In another embodiment, the present invention provides an isolated antibody or antigen-binding fragment thereof comprising, consisting essentially of, or consisting of an immunoglobulin light chain variable domain (VL domain), where at least one of the CDRs of the VL domain has an amino acid sequence that is identical to CDR1, CDR2 or CDR3 of SEQ ID NO:42.

In another embodiment, the present invention provides an isolated antibody or antigen-binding fragment thereof comprising, consisting essentially of, or consisting of an immunoglobulin light chain variable domain (VL domain), where at least one of the CDRs of the VL domain has an amino acid sequence that is identical to SEQ ID NO:46, SEQ ID NO: 47, or SEQ ID NO:48.

In a further embodiment, the present invention includes an isolated antibody or antigen-binding fragment thereof comprising, consisting essentially of, or consisting of a VL domain that has an amino acid sequence that is identical to SEQ ID NO:42, wherein an anti-VEGF antibody comprising the encoded VL domain specifically or preferentially binds to VEGF, more specifically, human VEGF.

Polypeptide sequences of the anti-VEGF antibodies or antigen binding molecules thereof including the following:

The H7230 and L7104 variable regions that have the following amino acid sequences (CDRs are underlined):

```
H7230 (SEQ ID NO: 41):
QVQLVQSGAELRKPGASVKISCKASGYSLTYYGMNWVRQAPGQGLEWMG
WINTFTGDSTYAQDFTGRFVFSLDTSVSTAYLQISSLKAEDMAMYYCAK
YPHYYGSSHWYFDVWGQGTTVTSS

L7104 (SEQ ID NO: 42):
EIVLTQSPATLSVSPGERATLSCRASQSVNSNLAWYQQKPGQAPRVLIY
GASTRATGIPARFSGSGSGTEFTLTISSLQSEDFAVYYCQQYSDIPWTF
GQGTKLEIK
```

The CDRs of MAb 7392 (comprising H7230 and L7104 variable regions) that have the following amino acid sequences:

```
VH-CDR1 (SEQ ID NO: 43):
GYSLTYYGMN

VH-CDR2 (SEQ ID NO: 44):
WINTFTGDSTYAQDFTG

VH-CDR3 (SEQ ID NO: 45):
YPHYYGSSHWYFDV

VL-CDR1 (SEQ ID NO: 46):
RASQSVNSNLA

VL-CDR2 (SEQ ID NO: 47):
GASTRAT

VL-CDR3 (SEQ ID NO: 48):
QQYSDIPWT
```

Suitable biologically active variants of the anti-VEGF antibodies of the invention can be used in the methods of the present invention. Such variants will retain the desired binding properties of the parent anti-VEGF antibody. Methods for making antibody variants are generally available in the art.

Methods for mutagenesis and nucleotide sequence alterations are well known in the art. See, for example, Walker and Gaastra, eds. (1983) Techniques in Molecular Biology (MacMillan Publishing Company, New York); Kunkel, Proc. *Natl. Acad. Sci. USA* 82:488-492 (1985); Kunkel et al., *Methods Enzymol.* 154:367-382 (1987); Sambrook et al. (1989) Molecular Cloning: A Laboratory Manual (Cold Spring Harbor, N.Y.); U.S. Pat. No. 4,873,192; and the references cited therein; herein incorporated by reference. Guidance as to appropriate amino acid substitutions that do not affect biological activity of the polypeptide of interest may be found in the model of Dayhoff et al. (1978) in Atlas of Protein Sequence and Structure (Natl. Biomed. Res. Found., Washington, D.C.), pp. 345-352, herein incorporated by reference in its entirety. The model of Dayhoff et al. uses the Point Accepted Mutation (PAM) amino acid similarity matrix (PAM 250 matrix) to determine suitable conservative amino acid substitutions. Conservative substitutions, such as exchanging one amino acid with another having similar properties, may be preferred. Examples of conservative amino acid substitutions as taught by the PAM 250 matrix of the Dayhoff et al. model include, but are not limited to, Gly↔Ala, Val↔Ile↔Leu, Asp↔Glu, Lys↔Arg, Asn↔Gln, and Phe↔Trp↔Tyr. Modifications are made such that variants continue to possess the desired properties, e.g., being capable of specifically binding to a VEGF, more specifically, human VEGF, e.g., secreted by a cell or attached by a membrane or extracellular matrix component and having VEGF blocking activity, as described herein. Any mutations made in the DNA encoding the variant polypeptide must not place the sequence out of reading frame and preferably will not create complementary regions that could produce secondary mRNA structure. See EP Patent Application Publication No. 75,444.

Methods for measuring anti-VEGF binding molecule, e.g., an antibody or antigen-binding fragment thereof, binding specificity include, but are not limited to, standard competitive binding assays, assays for monitoring immunoglobulin secretion by T cells or B cells, T cell proliferation assays, apoptosis assays, ELISA assays, and the like. See, for example, such assays disclosed in WO 93/14125; Shi et al., *Immunity* 13:633-642 (2000); Kumanogoh et al., *J Immunol* 169:1175-1181 (2002); Watanabe et al., *J Immunol* 167: 4321-4328 (2001); Wang et al., *Blood* 97:3498-3504 (2001); and Giraudon et al., *J Immunol* 172(2):1246-1255 (2004), all of which are herein incorporated by reference.

The % identity of a polypeptide discussed herein can be determined using methods and computer programs/software known in the art such as, but not limited to, the BESTFIT program (Wisconsin Sequence Analysis Package, Version 8 for Unix, Genetics Computer Group, University Research Park, 575 Science Drive, Madison, Wis. 53711). BESTFIT uses the local homology algorithm of Smith and Waterman (1981) *Adv. Appl. Math.* 2:482-489, to find the best segment of homology between two sequences. When using BESTFIT or any other sequence alignment program to determine whether a particular sequence is, for example, 95% identical to a reference sequence according to the present invention, the parameters are set, of course, such that the percentage of identity is calculated over the full length of the reference polypeptide sequence and that gaps in homology of up to 5% of the total number of amino acids in the reference sequence are allowed.

For purposes of the present invention, percent sequence identity may be determined using the Smith-Waterman homology search algorithm using an affine gap search with a gap open penalty of 12 and a gap extension penalty of 2, BLOSUM matrix of 62. The Smith-Waterman homology search algorithm is taught in Smith and Waterman (1981) *Adv. Appl. Math.* 2:482-489. A variant may, for example, differ from a reference anti-VEGF antibody (e.g., MAb 7392, comprising the variable region sequences of SEQ ID NO:41 and SEQ ID NO:42) by 5 or fewer amino acid residues, e.g., in the light or heavy chain framework regions.

The precise chemical structure of a polypeptide capable of specifically binding VEGF and retaining the desired VEGF blocking activity depends on a number of factors. As ionizable amino and carboxyl groups are present in the molecule, a particular polypeptide may be obtained as an acidic or basic salt, or in neutral form. All such preparations that retain their biological activity when placed in suitable environmental conditions are included in the definition of anti-VEGF antibodies as used herein. Further, the primary amino acid sequence of the polypeptide may be augmented by derivatization using sugar moieties (glycosylation) or by other supplementary molecules such as lipids, phosphate, acetyl groups and the like. It may also be augmented by conjugation with saccharides. Certain aspects of such augmentation are accomplished through post-translational processing systems of the producing host; other such modifications may be introduced in vitro. In any event, such modifications are included in the definition of an anti-VEGF antibody used herein so long as the desired properties of the anti-VEGF antibody are not destroyed. It is expected that such modifications may quantitatively or qualitatively affect the activity, either by enhancing or diminishing the activity of the polypeptide, in the various assays. Further, individual amino acid residues in the chain may be modified by oxidation, reduction, or other derivatization, and the polypeptide may be cleaved to obtain fragments that retain activity. Such alterations that do not destroy the desired properties (e.g., binding specificity for VEGF, binding affinity, and VEGF blocking activity) do not remove the polypeptide sequence from the definition of anti-VEGF antibodies of interest as used herein.

The art provides substantial guidance regarding the preparation and use of polypeptide variants. In preparing the anti-VEGF binding molecule, e.g., an antibody or antigen-binding fragment thereof, variants, one of skill in the art can readily determine which modifications to the native protein's nucleotide or amino acid sequence will result in a variant that is suitable for use as a therapeutically active component of a pharmaceutical composition used in the methods of the present invention.

The constant region of an anti-VEGF antibody may be mutated to alter effector function in a number of ways. For example, see U.S. Pat. No. 6,737,056B1 and U.S. Patent Application Publication No. 2004/0132101A1, which disclose Fc mutations that optimize antibody binding to Fc receptors.

In certain anti-VEGF antibodies, the Fc portion may be mutated to decrease effector function using techniques known in the art. For example, the deletion or inactivation (through point mutations or other means) of a constant region domain may reduce Fc receptor binding of the circulating modified antibody thereby increasing tumor localization. In other cases it may be that constant region modifications consistent with the instant invention moderate complement binding and thus reduce the serum half life and nonspecific association of a conjugated cytotoxin. Yet other modifications of the constant region may be used to modify disulfide linkages or oligosaccharide moieties that allow for enhanced localization due to increased antigen specificity or antibody flexibility. The resulting physiological profile, bioavailability and other biochemical effects of the modifications, such as tumor localization, biodistribution and serum half-life, may easily be measured and quantified using well known immunological techniques without undue experimentation.

Anti-VEGF antibodies of the invention also include derivatives that are modified, e.g., by the covalent attachment of any type of molecule to the antibody such that covalent attachment does not prevent the antibody from specifically binding to its cognate epitope. For example, but not by way of limitation, the antibody derivatives include antibodies that have been modified, e.g., by glycosylation, acetylation, pegylation, phosphorylation, amidation, derivatization by known protecting/blocking groups, proteolytic cleavage, linkage to a cellular ligand or other protein, etc. Any of numerous chemical modifications may be carried out by known techniques, including, but not limited to specific chemical cleavage, acetylation, formylation, etc. Additionally, the derivative may contain one or more non-classical amino acids.

A "conservative amino acid substitution" is one in which the amino acid residue is replaced with an amino acid residue having a side chain with a similar charge. Families of amino acid residues having side chains with similar charges have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Alternatively, mutations can be introduced randomly along all or part of the coding sequence, such as by saturation mutagenesis, and the resultant mutants can be screened for biological activity to identify mutants that retain activity (e.g., the ability to bind a VEGF polypeptide).

For example, it is possible to introduce mutations only in framework regions or only in CDR regions of an antibody molecule. Introduced mutations may be silent or neutral missense mutations, i.e., have no, or little, effect on an antibody's ability to bind antigen. These types of mutations may be useful to optimize codon usage, or improve a hybridoma's antibody production. Alternatively, non-neutral missense mutations may alter an antibody's ability to bind antigen. The location of most silent and neutral missense mutations is likely to be in the framework regions, while the location of most non-neutral missense mutations is likely to be in CDR, though this is not an absolute requirement. One of skill in the art would be able to design and test mutant molecules with desired properties such as no alteration in antigen binding activity or alteration in binding activity (e.g., improvements in antigen binding activity or change in antibody specificity). Following mutagenesis, the encoded protein may routinely be expressed and the functional and/or biological activity of the encoded protein, (e.g., ability to immunospecifically bind at least one epitope of a VEGF polypeptide) can be determined using techniques described herein or by routinely modifying techniques known in the art.

In certain embodiments, the anti-VEGF antibodies of the invention are generated, e.g., by V-gene replacement. V-gene replacement involves the use of a human monoclonal antibody discover platform, e.g., as described in US 2002-0123057 A1, incorporated herein by reference in its entirety, based on the monoclonal expression of recombinant antibodies in mammalian cells. As described in US 2002-0123057 A1, separate libraries of human heavy and light chain immunoglobulin variable genes have been constructed in a vaccinia virus-based vector by the method of "Trimolecular Recombination." Plasmid vectors incorporating constant regions of human heavy chain secreted gamma 1, human heavy chain membrane bound gamma 1, or human light chain were constructed to accommodate cloning human Ig variable region gene segments (VH, VK and VX) in frame. These vectors are based on the plasmid pH5/tk, in which a vaccinia early/late promoter and multiple cloning sites were inserted into the viral tk gene. The multiple cloning sites were modified appropriately in order to clone in a modified Ig secretory signal peptide and the constant regions of γ1-secreted or γ1-membrane immunoglobulin heavy chains, and K immunoglobulin light chains. The resulting vectors retain unique cloning sites for inserting the VH and VK variable region genes. Throughout this description VK is referred to as VL.

In order to take advantage of the increased diversity generated by random pairing of different heavy and light chains, independent libraries of heavy and light chains were constructed, allowing generation of libraries of sufficient complexity that appropriate VH/VL combinations would occur at a frequency that permits efficient isolation of antibodies with a desired specificity and affinity. The independent assortment of germline V (D) and J segments, as well as the random combinatorial association of VL and VH, provides substantial diversity. Further diversification occurs during the response to antigen by the process of somatic mutation. To take advantage of all diversification processes, libraries produced from four different human B cell sources can be used: 1) commercially obtained bone marrow-derived mRNA from large donor pools, 2) commercially available peripheral blood B cells isolated from cancer patients 3) commercially available peripheral blood B cells, and Bone Marrow from autoimmune patients (ex. Lupus), and 4) tonsil-derived germinal center B cells. Because heavy and light chains are randomly re-assorted in this system, it is possible to generate novel specificities that are more diverse than those of the antigen-driven B cells from which these V genes derive. Somatic hypermutation in the germinal centers and selection resulting from the disease states of the B cell donors contributes greatly to V gene diversity.

Mammalian cells infected with vaccinia immunoglobulin gene recombinant vectors produce fully functional, bivalent antibodies. As outlined above, Ig-H libraries have been generated in a vaccinia expression vector that encodes the secretory form of the human gamma 1 heavy chain constant region. Co-infection of cells with these immunoglobulin heavy chain gene libraries and light chain libraries results in expression, assembly and secretion of bivalent IgG1/L antibodies, permitting screening by ELISA. By infecting host cells with multiplicity of infection (moi)=1 for both Ig-H and Ig-L vaccinia recombinants, each cell is on average infected with one Ig-H and one Ig-L recombinant vaccinia virus and thus expresses a single monoclonal antibody.

Hybridoma technology has been used to identify a number of rodent antibodies with specificity, affinity and functional activity towards important drug targets. For drug development these antibodies are often chimerized or humanized, with the attendant risk of immunogenicity and potential loss of affinity. The V gene replacement strategy has been applied to use of vaccinia virus expressed antibody libraries for conversion of rodent antibodies into fully human or mostly human antibodies.

The concept of V gene replacement in this application is to use a non-human antibody as a template and, through a two-step process, to identify human V genes that can replace the non-human V genes, while still retaining affinity and epitope specificity. The V gene replacement method is thus an alternative to traditional CDR grafted humanization. This method has several advantages compared to the more traditional humanization methods:

(i) V gene replacement results in the selection of fully human antibodies, while retaining the epitope specificity of the non-human MAb. In principle, these antibodies should have a lower risk of immunogenicity compared to CDR grafted and framework modified antibodies that retain significant amounts of murine sequences.

(ii) V gene replacement results in the selection of multiple antibodies. This allows for the selection of lead antibodies derived from distinct VH and VL germline genes with different biochemical properties including CDR sequences, expression levels, pI, etc.

(iii) V gene replacement can result in the selection of antibodies with better affinity and functional activity than the original non-human antibody.

In the first step of the V gene replacement method, the V genes from the non-human antibody are isolated and engineered to create chimeric heavy and light chains. The non-human Ig-H is paired with a library of human Ig-L and screened for specific binding to antigen. This initial selection yields a panel of hybrid antibodies comprising chimeric Ig-H and human Ig-L. The selected human Ig-Ls are then paired with a library of human Ig-H and selected for binding to antigen. Parallel selections can also be carried out starting with the non-human Ig-L to select human Ig-H, and then using the selected Ig-H to select human Ig-L. The human Ig-L selected with the chimeric Ig-H, and the human Ig-H selected with the chimeric Ig-L can also be cross-paired. The end result of these selection strategies is that panels of human antibodies that bind to the same antigen as the original non-human antibody are isolated. In most cases, the selected human antibodies recognize the same epitope as the original non-human antibody. If necessary, the first generation human antibodies can be affinity improved through either additional rounds of V gene replacement, or through mutagenesis Anti-VEGF antibodies (e.g., MAb 7392) may be selected based on the sustained or improved binding affinity and/or anti-VEGF activity that is imparted to an anti-VEGF antibody compared to a humanized or murine antibody to VEGF. "Anti-VEGF activity" or "VEGF blocking activity" can include activity that modulates one or more of the following activities associated with VEGF: angiogenesis; binding to cell VEGF receptors, including VEGFR1 and VEGFR2; modulating phosphorylation of VEGFR2; or any other activity association with soluble VEGF or VEGF that is bound, e.g., to the extracellular matrix. Anti-VEGF activity can also be attributed to a decrease in incidence or severity of diseases associated with VEGF expression, including, but not limited to, various types of neoplastic disorders, including solid tumors and hematological malignancies, autoimmune diseases, intraocular diseases, and inflammatory diseases. Further optimizing modifications may involve replacement of amino acid residues within one or more CDR and/or framework region such that an anti-VEGF antibody retains specificity for the VEGF antigen and has improved binding affinity and/or improved anti-VEGF activity.

VI. Treatment Methods Using Therapeutic Anti-SEMA4D and Anti-VEGF Antibodies

Methods of the invention are directed to the use of anti-SEMA4D or anti-Plexin-B1 and anti-VEGF or anti-VEGFR2 binding molecules, e.g., antibodies, including antigen-binding fragments, variants, and derivatives thereof, to inhibit angiogenesis in a subject in need of such inhibition, i.e., a cancer patient or patient with wet age-related macular degeneration (AMD). Though the following discussion refers to administration of an anti-SEMA4D and anti-VEGF antibody, the methods described herein are equally applicable to the antigen-binding fragments, variants, and derivatives of these antibodies that retain the desired properties of the antibodies of the invention, e.g., capable of specifically binding SEMA4D or VEGF, e.g., human, mouse, or human and mouse SEMA4D or VEGF, having SEMA4D or VEGF neutralizing activity, and/or blocking the interaction of SEMA4D and VEGF with its receptors. In some embodiments, bispecific antibodies may be used. A bispecific antibody is an artificial protein that is composed of fragments of two different monoclonal antibodies and consequently binds to two different types of antigen. In an embodiment, one arm (i.e., Fab region) of the antibody is capable of specifically binding SEMA4D and the other arm is capable of specifically binding VEGF. Variations on the bispecific antibody format are contemplated within the scope of the present invention. Bispecific antibodies may be generated using techniques that are well known in the art for example, see, for example, Ghayur et al., Expert Review of Clinical Pharmacology 3.4 (July 2010): p491; Lu et al., J. Biological Chemistry Vol. 280, No. 20, p. 19665-19672 (2005); Marvin et al., Acta Pharmacologic Sinica 26(6):649-658 (2005); and Milstein C et al., Nature 1983; 305: 537-40; 30 Brennan M et al., Science 1985; 229: 81-3; Thakur et al., Curr Opin Mol Ther. 2010 June; 12(3):340-9; and U.S. Patent Publication No. 2007/0004909.

It should also be appreciated that the methods described herein are also applicable to the substitution of anti-Plexin-B1 binding molecules for anti-SEMA4D antibody and/or the substitution of anti-VEGFR2 binding molecules for anti-VEGF antibody. In some embodiments, an anti-Plexin-B1 binding molecule can be used to inhibit the interaction of SEMA4D with Plexin-B1 by blocking binding of SEMA4D to Plexin-B1 and/or by preventing activation of Plexin-B1 by SEMA4D. In other embodiments, an anti-VEGFR2 binding molecule can be used to inhibit the interaction of VEGF and VEGFR2 by blocking binding of VEGF to its receptor (i.e., VEGFR2). It should be noted that any combination of anti-SEMA4D or anti-Plexin-B1 and anti-VEGF or anti-VEGFR2 binding molecules can be used to inhibit angiogenesis. In one embodiment, an anti-SEMA4D and anti-VEGF binding molecule can be used. In another embodiment, an anti-SEMA4D and anti-VEGFR2 binding molecule can be used. In another embodiment, an anti-Plexin-B1 and anti-VEGFR2 binding molecule can be used. In another embodiment, an anti-Plexin-B1 and anti-VEGF binding molecule can be used. In each of the above embodiments, the two recited binding specificities may be combined either as separate bivalent antibodies or in the separate univalent arms of a bispecific antibody.

In one embodiment, treatment includes the application or administration of an anti-SEMA4D and anti-VEGF binding molecule, e.g., an antibody or antigen binding fragment thereof as described herein to a patient, or application or administration of the anti-SEMA4D and anti-VEGF binding molecule to an isolated tissue or cell line from a patient, where the patient has a disease, a symptom of a disease, or a predisposition toward a disease. In another embodiment, treatment is also intended to include the application or administration of a pharmaceutical composition comprising the anti-SEMA4D and anti-VEGF binding molecules, e.g., an antibody or antigen binding fragment thereof to a patient, or application or administration of a pharmaceutical composition comprising the anti-SEMA4D and anti-VEGF binding molecule to an isolated tissue or cell line from a patient, where the patient has a disease, a symptom of a disease, or a predisposition toward a disease The anti-SEMA4D and anti-VEGF binding molecules, e.g., antibodies or binding fragments thereof as described herein are useful for the treatment of various malignant and non-malignant tumors, in particular the inhibition of angiogenesis that supports growth of a primary tumor or inhibition of metastases. By "anti-tumor activity" is intended a reduction in the rate of SEMA4D and VEGF production or accumulation associated directly with the tumor or indirectly with stromal cells of the tumor environment, and hence a decline in growth rate of an existing tumor or in a tumor that arises during therapy, and/or destruction of existing neoplastic (tumor) cells or newly formed neoplastic cells, and hence a decrease in the overall size of a tumor and/or the number of metastatic sites during therapy. For example, therapy with at least one anti-SEMA4D and one anti-VEGF antibody causes a physiological response, for example, a reduction in angiogenesis, that is beneficial with respect to treatment of disease states associated with SEMA4D and VEGF-expressing cells in a human.

In one embodiment, the invention relates to the use of anti-SEMA4D and anti-VEGF binding molecules, e.g., antibodies or antigen-binding fragments, variants, or derivatives thereof, as a medicament, in particular for use in the treatment or prophylaxis of cancer or for use in a precancerous condition or lesion to inhibit, reduce, prevent, or minimalize the formation of new blood vessels. In certain embodiments, an anti-SEMA4D and anti-VEGF binding molecules, e.g., an antibody or binding fragment thereof, of the present invention can also be used to inhibit angiogenesis for the treatment of pathological conditions dependent upon the formation of new blood vessels, including tumor development and macular degeneration. Angiogenesis is a complex multistep morphogenetic event during which endothelial cells, stimulated by major determinants of vascular remodeling, dynamically modify their cell-to-cell and cell-to-matrix contacts and move directionally to be reorganized into a mature vascular tree (Bussolino et al., *Trends Biochem Sci.* 22:251-256 (1997); Risau, *Nature* 386:671-674 (1997); Jain, *Nat. Med.* 9:685-693 (2003)). The formation of new blood vessels is a key step during embryo development, but it also occurs in adults in physiologic and in pathologic conditions, such as retinopathy, rheumatoid arthritis, ischemia, and particularly tumor growth and metastasis (Carmeliet, *Nat. Med.* 9:653-660 (2003)). This pathological formation of new blood vessels is also herein referred to as "invasive angiogenesis."

In accordance with the methods of the present invention, at least one anti-SEMA4D and one anti-VEGF binding molecule, e.g., an antibody or antigen binding fragment, variant, or derivative thereof, as defined elsewhere herein can be used to promote a positive therapeutic response with respect to a malignant human cell. By "positive therapeutic response" with respect to cancer treatment is intended an improvement in the disease in association with the anti-tumor activity of these binding molecules, e.g., antibodies or fragments thereof, and/or an improvement in the symptoms associated with the disease. That is, a decrease in tumor vasculature, a reduction in tumor size, an anti-proliferative effect, the prevention of further tumor outgrowths, a reduction in the number of cancer cells, and/or a decrease in one or more symptoms associated with the disease can be observed. In particular, the methods provided herein are directed to inhibiting, preventing, reducing, alleviating, or lessening the formation of new blood cells and/or new metastatic sites in a patient. In addition to these positive therapeutic responses, the subject undergoing therapy with the anti-SEMA4D and anti-VEGF binding molecules, e.g., an antibody or antigen-binding fragment, variant, or derivative thereof, may experience the beneficial effect of an improvement in the symptoms associated with the disease.

Tumor response can be assessed for changes in tumor morphology (i.e., overall tumor burden, tumor cell count, and the like) using screening techniques such as bioluminescent imaging, for example, luciferase imaging, bone scan imaging, and tumor biopsy sampling including bone marrow aspiration (BMA). In addition to these positive therapeutic responses, the subject undergoing therapy with the anti-SEMA4D and anti-VEGF binding molecules, e.g., an antibody or antigen-binding fragment, variant, or derivative thereof, can experience the beneficial effect of an improvement in the symptoms associated with the disease.

Clinical response can be assessed using screening techniques such as magnetic resonance imaging (MRI) scan, x-radiographic imaging, computed tomographic (CT) scan, flow cytometry or fluorescence-activated cell sorter (FACS) analysis, histology, gross pathology, and blood chemistry, including but not limited to changes detectable by ELISA, RIA, chromatography, and the like.

The anti-SEMA4D and anti-VEGF binding molecules, e.g., antibodies or antigen binding fragments, variants, or derivatives thereof can be used in combination with at least one or more other cancer therapy agents, including, but not limited to, surgery or surgical procedures (e.g. splenectomy, hepatectomy, lymphadenectomy, leukophoresis, bone marrow transplantation, and the like); radiation therapy; chemotherapy, optionally in combination with autologous bone marrow transplant, or other cancer therapy; where the additional cancer therapy is administered prior to, during, or subsequent to the anti-SEMA4D and anti-VEGF binding molecules, e.g., antibody or antigen binding fragment, variant, or derivative thereof, therapy. Thus, where the combined therapies comprise administration of an anti-SEMA4D and anti-VEGF binding molecules, e.g., an antibody or antigen binding fragment, variant, or derivative thereof, in combination with administration of another therapeutic agent, as with chemotherapy, radiation therapy, other anti-cancer antibody therapy, small molecule-based cancer therapy, or vaccine/immunotherapy-based cancer therapy, the methods of the invention encompass co-administration, using separate formulations or a single pharmaceutical formulation, with simultaneous or consecutive administration in either order.

VII. Pharmaceutical Compositions and Administration Methods

Methods of preparing and administering anti-SEMA4D and anti-VEGF binding molecules, e.g., antibodies, or antigen-binding fragments, variants, or derivatives thereof to a subject in need thereof are well known to or are readily determined by those skilled in the art. The route of administration of the anti-SEMA4D binding molecule, e.g, antibody, or antigen-binding fragment, variant, or derivative thereof, can be, for example, oral, parenteral, by inhalation or topical. The term parenteral as used herein includes, e.g., intravenous, intraarterial, intraperitoneal, intramuscular, subcutaneous, rectal, or vaginal administration. While all these forms of administration are clearly contemplated as being within the scope of the invention, an example of a form for administration would be a solution for injection, in particular for intravenous or intraarterial injection or drip. A suitable pharmaceutical composition for injection can comprise a buffer (e.g. acetate, phosphate or citrate buffer), a surfactant (e.g. polysorbate), optionally a stabilizer agent (e.g. human albumin), etc. However, in other methods compatible with the teachings herein, anti-SEMA4D and anti-VEGF binding molecules, e.g., antibodies, or antigen-binding fragments, variants, or derivatives thereof can be delivered directly to the site of the adverse cellular population thereby increasing the exposure of the diseased tissue to the therapeutic agent.

As discussed herein, anti-SEMA4D and anti-VEGF binding molecules, e.g., antibodies, or antigen-binding fragments, variants, or derivatives thereof can be administered in a pharmaceutically effective amount for the in vivo treatment of diseases such as neoplastic disorders, including solid tumors. In this regard, it will be appreciated that the disclosed binding molecules can be formulated so as to facilitate administration and promote stability of the active agent. In certain embodiments, pharmaceutical compositions in accordance with the present invention comprise a pharmaceutically acceptable, non-toxic, sterile carrier such as physiological saline, non-toxic buffers, preservatives and the like. For the purposes of the instant application, a pharmaceutically effective amount of an anti-SEMA4D and anti-VEGF binding molecules, e.g., an antibody, or antigen-binding fragment, variant, or derivative thereof, shall be held to mean an amount sufficient to achieve effective binding to a target and to achieve a benefit, i.e., to inhibit angiogenesis in a cancer patient.

The pharmaceutical compositions used in this invention comprise pharmaceutically acceptable carriers, including, e.g., ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol, and wool fat.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include, e.g., water, alcoholic/aqueous solutions, emulsions or suspensions, including saline and buffered media. In the subject invention, pharmaceutically acceptable carriers include, but are not limited to, 0.01-0.1 M and preferably 0.05 M phosphate buffer or 0.8% saline. Other common parenteral vehicles include sodium phosphate solutions, Ringer's dextrose, dextrose and sodium chloride, lactated Ringer's, or fixed oils. Intravenous vehicles include fluid and nutrient replenishers, electrolyte replenishers, such as those based on Ringer's dextrose, and the like. Preservatives and other additives may also be present such as, for example, antimicrobials, antioxidants, chelating agents, and inert gases and the like.

More particularly, pharmaceutical compositions suitable for injectable use include sterile aqueous solutions (where water soluble) or dispersions and sterile powders for the extemporaneous preparation of sterile injectable solutions or dispersions. In such cases, the composition must be sterile and should be fluid to the extent that easy syringability exists. It should be stable under the conditions of manufacture and storage and will preferably be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Suitable formulations for use in the therapeutic methods disclosed herein are described in Remington's Pharmaceutical Sciences (Mack Publishing Co.) 16th ed. (1980).

Prevention of the action of microorganisms can be achieved by various antibacterial and antifungal agents, for example, parabens, chlorobutanol, phenol, ascorbic acid, thimerosal and the like. In many cases, it will be preferable to include isotonic agents, for example, sugars, polyalcohols, such as mannitol, sorbitol, or sodium chloride in the composition. Prolonged absorption of the injectable compositions can be brought about by including in the composition an agent which delays absorption, for example, aluminum monostearate and gelatin.

In any case, sterile injectable solutions can be prepared by incorporating an active compound (e.g., an anti-SEMA4D or anti-VEGF antibody, or antigen-binding fragment, variant, or derivative thereof, by itself or in combination with other active agents) in the required amount in an appropriate solvent with one or a combination of ingredients enumerated herein, as required, followed by filtered sterilization. Generally, dispersions are prepared by incorporating the active compound into a sterile vehicle, which contains a basic dispersion medium and the required other ingredients from those enumerated above. In the case of sterile powders for the preparation of sterile injectable solutions, the preferred methods of preparation are vacuum drying and freeze-drying, which yields a powder of an active ingredient plus any additional desired ingredient from a previously sterile-filtered solution thereof. The preparations for injections are processed, filled into containers such as ampoules, bags, bottles, syringes or vials, and sealed under aseptic conditions according to methods known in the art. Further, the preparations may be packaged and sold in the form of a kit. Such articles of manufacture can have labels or package inserts indicating that the associated compositions are useful for treating a subject suffering from, or predisposed to a disease or disorder.

Parenteral formulations can be a single bolus dose, an infusion or a loading bolus dose followed with a maintenance dose. These compositions can be administered at specific fixed or variable intervals, e.g., once a day, or on an "as needed" basis.

Certain pharmaceutical compositions used in this invention can be orally administered in an acceptable dosage form including, e.g., capsules, tablets, aqueous suspensions or solutions. Certain pharmaceutical compositions also can be administered by nasal aerosol or inhalation. Such compositions can be prepared as solutions in saline, employing benzyl alcohol or other suitable preservatives, absorption promoters to enhance bioavailability, and/or other conventional solubilizing or dispersing agents.

The amount of an anti-SEMA4D and anti-VEGF binding molecule, e.g., antibody, or fragment, variant, or derivative thereof, to be combined with the carrier materials to produce a single dosage form will vary depending upon the host treated and the particular mode of administration. The composition can be administered as a single dose, multiple doses or over an established period of time in an infusion. Dosage regimens also can be adjusted to provide the optimum desired response (e.g., a therapeutic or prophylactic response).

In keeping with the scope of the present disclosure, anti-SEMA4D antibodies, or antigen-binding fragments, variants, or derivatives thereof can be administered to a human or other animal in accordance with the aforementioned methods of treatment in an amount sufficient to produce a therapeutic effect. The anti-SEMA4D antibodies, or antigen-binding fragments, variants or derivatives thereof can be administered to such human or other animal in a conventional dosage form prepared by combining the antibody of the invention with a conventional pharmaceutically acceptable carrier or diluent according to known techniques. It will be recognized by one of skill in the art that the form and character of the pharmaceutically acceptable carrier or diluent is dictated by the amount of active ingredient with which it is to be combined, the route of administration and other well-known variables. Those skilled in the art will further appreciate that a cocktail comprising one or more species of anti-SEMA4D and anti-VEGF binding molecules, e.g., antibodies, or antigen-binding fragments, variants, or derivatives thereof, of the invention can be used.

By "therapeutically effective dose or amount" or "effective amount" is intended an amount of anti-SEMA4D and anti-VEGF binding molecule, e.g., antibody or antigen binding fragment, variant, or derivative thereof, that when administered brings about a positive therapeutic response with respect to treatment of a patient with a disease to be treated, e.g., an inhibition of angiogenesis in the patient.

Therapeutically effective doses of the compositions of the present invention, for the inhibition of angiogenesis, vary depending upon many different factors, including means of administration, target site, physiological state of the patient, whether the patient is human or an animal, other medications administered, and whether treatment is prophylactic or therapeutic. In certain embodiments the patient is a human, but non-human mammals including transgenic mammals can also be treated. Treatment dosages may be titrated using routine methods known to those of skill in the art to optimize safety and efficacy.

The amount of at least one anti-SEMA4D and anti-VEGF binding molecule, e.g., antibody or binding fragment, variant, or derivative thereof, to be administered is readily determined by one of ordinary skill in the art without undue experimentation given the disclosure of the present invention. Factors influencing the mode of administration and the respective amount of at least one anti-SEMA4D and one anti-VEGF binding molecule, e.g., antibody, antigen-binding fragment, variant or derivative thereof include, but are not limited to, the severity of the disease, the history of the disease, the potential for angiogenesis, and the age, height, weight, health, and physical condition of the individual undergoing therapy. Similarly, the amount of anti-SEMA4D and anti-VEGF binding molecule, e.g., antibody, or fragment, variant, or derivative thereof, to be administered will be dependent upon the mode of administration and whether the subject will undergo a single dose or multiple doses of this agent.

The invention also provides for the use of an anti-SEMA4D and anti-VEGF binding molecule, e.g., antibody of the invention, or antigen-binding fragment, variant, or derivative thereof, in the manufacture of a medicament for treating a subject for treating a cancer, wherein the medicament is used in a subject that has been pretreated with at least one other therapy. By "pretreated" or "pretreatment" is intended the subject has received one or more other therapies (e.g., been treated with at least one other cancer therapy) prior to receiving the medicament comprising the anti-SEMA4D and anti-VEGF binding molecule, e.g., antibody or antigen-binding fragment, variant, or derivative thereof. "Pretreated" or "pretreatment" includes subjects that have been treated with at least one other therapy within 2 years, within 18 months, within 1 year, within 6 months, within 2 months, within 6 weeks, within 1 month, within 4 weeks, within 3 weeks, within 2 weeks, within 1 week, within 6 days, within 5 days, within 4 days, within 3 days, within 2 days, or even within 1 day prior to initiation of treatment with the medicament comprising the anti-SEMA4D and anti-VEGF binding molecule, for example, the monoclonal antibody VX15/2503 disclosed herein, or antigen-binding fragment, variant, or derivative thereof. It is not necessary that the subject was a responder to pretreatment with the prior therapy or therapies. Thus, the subject that receives the medicament comprising the anti-SEMA4D and anti-VEGF binding molecule, e.g., an antibody or antigen-binding fragment, variant, or derivative thereof could have responded, or could have failed to respond (e.g., the cancer was refractory), to pretreatment with the prior therapy, or to one or more of the prior therapies where pretreatment comprised multiple therapies. Examples of other cancer therapies for which a subject can have received pretreatment prior to receiving the medicament comprising the anti-SEMA4D and anti-VEGF binding molecule, e.g., antibody or antigen-binding fragment, variant, or derivative thereof include, but are not limited to, surgery; radiation therapy; chemotherapy, optionally in combination with autologous bone marrow transplant, where suitable chemotherapeutic agents include, but are not limited to, those listed herein above; other anti-cancer monoclonal antibody therapy; small molecule-based cancer therapy, including, but not limited to, the small molecules listed herein above; vaccine/immunotherapy-based cancer therapies; steroid therapy; other cancer therapy; or any combination thereof.

The practice of the present invention will employ, unless otherwise indicated, conventional techniques of cell biology, cell culture, molecular biology, transgenic biology, microbiology, recombinant DNA, and immunology, which are within the skill of the art. Such techniques are explained fully in the literature. See, for example, Sambrook et al., ed. (1989) Molecular Cloning A Laboratory Manual (2nd ed.; Cold Spring Harbor Laboratory Press); Sambrook et al., ed. (1992) Molecular Cloning: A Laboratory Manual, (Cold Springs Harbor Laboratory, NY); D. N. Glover ed., (1985) DNA Cloning, Volumes I and II; Gait, ed. (1984) Oligonucleotide Synthesis; Mullis et al. U.S. Pat. No. 4,683,195; Hames and Higgins, eds. (1984) Nucleic Acid Hybridization; Hames and Higgins, eds. (1984) Transcription And Translation; Freshney (1987) Culture Of Animal Cells (Alan R. Liss, Inc.); Immobilized Cells And Enzymes (IRL Press) (1986); Perbal (1984) A Practical Guide To Molecular Cloning; the treatise, Methods In Enzymology (Academic Press, Inc., N.Y.); Miller and Calos eds. (1987) Gene Transfer Vectors For Mammalian Cells, (Cold Spring Harbor Laboratory); Wu et al., eds., Methods In Enzymology, Vols. 154 and 155; Mayer and Walker, eds. (1987) Immunochemical Methods In Cell And Molecular Biology (Academic Press, London); Weir and Blackwell, eds., (1986) Handbook Of Experimental Immunology, Volumes I-IV; Manipulating the Mouse Embryo, Cold Spring Harbor Laboratory Press, Cold Spring Harbor, N.Y., (1986); and in Ausubel et al. (1989) Current Protocols in Molecular Biology (John Wiley and Sons, Baltimore, Md.).

General principles of antibody engineering are set forth in Borrebaeck, ed. (1995) Antibody Engineering (2nd ed.; Oxford Univ. Press). General principles of protein engineering are set forth in Rickwood et al., eds. (1995) Protein Engineering, A Practical Approach (IRL Press at Oxford Univ. Press, Oxford, Eng.). General principles of antibodies and antibody-hapten binding are set forth in: Nisonoff (1984) Molecular Immunology (2nd ed.; Sinauer Associates, Sunderland, Mass.); and Steward (1984) Antibodies, Their Structure and Function (Chapman and Hall, New York, N.Y.). Additionally, standard methods in immunology known in the art and not specifically described are generally followed as in Current Protocols in Immunology, John Wiley & Sons, New York; Stites et al., eds. (1994) Basic and Clinical Immunology (8th ed; Appleton & Lange, Norwalk, Conn.) and Mishell and Shiigi (eds) (1980) Selected Methods in Cellular Immunology (W.H. Freeman and Co., NY).

Standard reference works setting forth general principles of immunology include Current Protocols in Immunology, John Wiley & Sons, New York; Klein (1982) J., Immunology: The Science of Self-Nonself Discrimination (John Wiley & Sons, NY); Kennett et al., eds. (1980) Monoclonal Antibodies, Hybridoma: A New Dimension in Biological Analyses (Plenum Press, NY); Campbell (1984) "Monoclonal Antibody Technology" in Laboratory Techniques in Biochemistry and Molecular Biology, ed. Burden et al., (Elsevere, Amsterdam); Goldsby et al., eds. (2000) Kuby Immunnology (4th ed.; H. Freemand & Co.); Roitt et al. (2001) Immunology (6th ed.; London: Mosby); Abbas et al. (2005) Cellular and Molecular Immunology (5th ed.; Elsevier Health Sciences Division); Kontermann and Dubel (2001) Antibody Engineering (Springer Verlan); Sambrook and Russell (2001) Molecular Cloning: A Laboratory Manual (Cold Spring Harbor Press); Lewin (2003) Genes VIII (Prentice Hall2003); Harlow and Lane (1988) Antibodies: A Laboratory Manual (Cold Spring Harbor Press); Dieffenbach and Dveksler (2003) PCR Primer (Cold Spring Harbor Press).

All of the references cited above, as well as all references cited herein, are incorporated herein by reference in their entireties.

The following examples are offered by way of illustration and not by way of limitation.

EXAMPLES

The following examples demonstrate the efficacy of anti-SEMA4D antibody VX15/2503 and anti-VEGF antibody on inhibiting the growth of HN6 head and neck tumors in mice.

Example 1

Experimental Design

The basic experimental design is as follows. Tumor cells were implanted subcutaneously into both flanks of athymic nude mice. The tumor bearing nude mice were divided into four groups of seven mice each with each mouse having two tumors. The first group (control group) was treated with IgG isotype control MAb 2955. The second group was treated with anti-SEMA4D antibody VX15/2503. The third group was treated with an anti-VEGF antibody (Mouse IgG2A MAb 2931, which is a human VEGF MAb, Mouse IgG2A, Catalog #MAB2931; R&D Systems). The fourth group was treated with a combination of anti-SEMA4D antibody (VX15/2503) and anti-VEGF antibody (Mouse IgG2A MAb 2931). The treatment started two days post tumor graft. Mice were treated once a week with 1.0 mg (approximately 50 mg/kg) of monoclonal antibody via intraperitoneal (IP) injection for three weeks.

Example 2

Primary Tumor Growth

Primary tumor growth was measured by calipers up to sacrifice, which measurements were used to calculate tumor volume. The animals treated with VX15/2503 alone showed a reduction in primary tumor volume at the time of sacrifice over the control animals, with the difference being statistically significant ($P<0.0001$). The animals treated with anti-VEGF (Mouse IgG2A MAb 2931) alone also showed a reduction in primary tumor volume at the time of sacrifice over the control animals, with the difference being statistically significant ($P<0.0001$). In addition, an additive effect on reduction of the tumor volume was seen when anti-SEMA4D antibody (VX15/2503) was used in combination with anti-VEGF antibody, with the difference being statistically significant ($P<0.0001$). Statistical analysis was conducted using Two-way Analysis of Variance (ANOVA), comparing tumor growth in each group to control antibody. T-test of final tumor volumes of resected tumors also resulted in statistically significant differences ($P<0.0001$). The results are shown in FIG. 1, which shows the mean tumor volume among the four groups. FIG. 2 shows representative photographs for the extracted tumors.

Example 3

Primary Tumor Vascular Density

The vascular density of the tumors was also measured. Vascular density was measured as vessels per 10 hpf (high power field). Treatment with either VX15/2503 or anti-VEGF (Mouse IgG2A MAb 2931) individually resulted in a decrease in vascular density, as compared to the control group. Treatment with anti-SEMA4D antibody (VX15/2503) in combination with anti-VEGF antibody resulted in a greater reduction in vascular density (**$P<0.01$), as compared to the control group as well as either VX15/2503 (*$P<0.05$) or anti-VEGF (*$P<0.05$) alone. The results are shown graphically in FIG. 3.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims and list of embodiments disclosed herein. Although specific terms are employed herein, they are used in a generic and descriptive sense only and not for purposes of limitation.

---

What is claimed is:

1. A method for inhibiting angiogenesis in a human subject, comprising administering to the subject an effective amount of a first isolated binding molecule comprising a heavy chain variable region (VH) polypeptide comprising VH-CDR1, VH-CDR2, and VH-CDR3 amino acid sequences comprising SEQ ID NOs: 6, 7, and 8, respectively, and a light chain variable region (VL) polypeptide comprising VL-CDR1, VL-CDR2, and VL-CDR3 amino acid sequences comprising SEQ ID NOs: 14, 15 and 16, respectively, wherein the first isolated binding molecule specifically binds to semaphorin-4D (SEMA4D) and an effective amount of a second isolated binding molecule which specifically binds to VEGF and inhibits the interaction of VEGF with a VEGF receptor.

2. The method of claim 1, wherein the first binding molecule hibits SEMA4D interaction with plexin-B1.

3. The method of claim 1, wherein the first binding molecule hibits SEMA4D-mediated plexin B1 signal transduction.

4. The method of claim 1, wherein the first isolated binding molecule specifically binds to the same SEMA4D epitope as a reference monoclonal antibody selected from the group consisting of VX15/2503, comprising a heavy chain variable domain (VH) and a light chain variable domain (VL) wherein the VH comprises the amino acid sequence of SEQ ID NO: 9 and the VL comprises the amino acid sequence of SEQ ID NO: 17, or monoclonal antibody 67, comprising a heavy chain variable domain (VH) and a light chain variable domain (VL) wherein the VH comprises the amino acid sequence of SEQ ID NO: 10 and the VL comprises the amino acid sequence of SEQ ID NO: 18.

5. The method of claim 1, wherein the first isolated binding molecule comprises an antibody or antigen-binding fragment thereof.

6. The method of claim 5, wherein the antibody or antigen-binding fragment thereof is monoclonal antibody VX15/2503, comprising a heavy chain variable domain (VH) and a light chain variable domain (VL) wherein the VH comprises the amino acid sequence of SEQ ID NO: 9 and the VL comprises the amino acid sequence of SEQ ID NO: 17, or monoclonal antibody 67, composing a heavy chain variable domain (VH) and a light chain variable domain (VL) wherein the VH comprises the amino acid sequence of SEQ ID NO: 10 and the VL comprises the amino acid sequence of SEQ ID NO: 18.

7. The method of claim 1 wherein the first isolated binding molecule competitively inhibits a reference monoclonal antibody selected from the group consisting of VX15/2503, comprising a heavy chain variable domain (VH) and a light chain variable domain (VL) wherein the VH comprises the amino acid sequence of SEQ ID NO: 9 and the VL comprises the amino acid sequence of SEQ ID NO: 17, and monoclonal antibody 67, comprising a heavy chain variable domain (VH) and a light chain variable domain (VL) wherein the VH comprises the amino acid sequence of SEQ ID NO: 10 and the VL comprises the amino acid sequence of SEQ ID NO: 18, from specifically binding to SEMA4D.

8. The method of claim 1, wherein the VEGF receptor is VEGFR1 or VEGFR2.

9. The method of claim 1, wherein the second binding molecule inhibits phosphorylation of VEGFR2 by VEGF.

10. The method of claim 1, wherein the inhibition of angiogenesis occurs independently of metastases inhibition.

11. The method of claim 1, wherein the subject has cancer.

12. The method of claim 11, wherein the cancer is selected from the group consisting of sarcoma, breast, ovarian, head and neck, pancreatic, prostate, lung, kidney, colorectal, brain, gastric, bladder, esophageal and a combination thereof.

13. A method of alleviating cancer in a human subject, comprising administering to the subject an effective amount of a first isolated binding molecule comprising a heavy chain variable region (VH) polypeptide comprising VH-CDR1, VH-CDR2, and VH-CDR3 amino acid sequences comprising SEQ ID NOs: 6, 7, and 8, respectively, and a light chain variable region (VL) polypeptide comprising VL-CDR1, VL-CDR2, and VL-CDR3 amino acid sequences comprising SEQ ID NOs: 14, 15, and 16, respectively, wherein the first isolated binding molecule specifically binds to semaphorin-4D (SEMA4D) and an effective amount of a second isolated binding molecule which specifically binds to VEGF and inhibits the interaction of VEGF with a VEGF receptor wherein the first isolated binding molecule and second isolated binding molecule act to inhibit angiogenesis.

14. A method for inhibiting angiogenesis in a human subject, comprising administering to the subject an effective amount of a first isolated binding molecule comprising a heavy chain variable region (VH) polypeptide comprising VH-CDR1, VH-CDR2, and VH-CDR3 amino acid sequences comprising SEQ ID NOs: 6, 7, and 8, respectively, and a light chain variable region (VL) polypeptide comprising VL-CDR1, VL-CDR2, and VL-CDR3 amino acid sequences comprising SEQ ID NOs: 14, 15, and 16, respectively, wherein the first isolated binding molecule inhibits interaction of semaphorin-4D (SEMA4D) with Plexin-B1 and an effective amount of a second isolated binding molecule whirl inhibits interaction of VEGF with VEGFR2.

15. The method of claim 14, wherein the second isolated binding molecule is selected from the group consisting of an anti-VEGF and an anti-VEGFR2 binding molecule.

16. The method of claim 14, wherein the subject has cancer.

17. The method of any one of claims 1 to 7, 8-12, 13-14, 15 or 16, wherein the first binding molecule and the second binding molecule are administered separately or concurrently.

18. The method of claim 1 wherein the of the VH of the first isolated binding molecule comprises an amino acid sequence at least 90% identical to SEQ ID NO: 9 or SEQ ID NO: 10.

19. The method of claim 1, wherein the VL of the first isolated binding molecule comprises an amino acid sequence at least 90% identical to SEQ ID NO: 17 or SEQ ID NO: 18.

20. The method of claim 11, wherein the inhibition of angiogenesis results in a decrease in vascular density in the cancer.

21. The method of claim 18, wherein the VH of the first isolated binding molecule comprises the amino acid sequence of SEQ ID NO: 9 or SEQ ID NO: 10.

22. The method of claim 19, wherein the VL of the first isolated binding molecule comprises the amino acid sequence of SEQ ID NO: 17 or SEQ ID NO: 18.

* * * * *